US012714694B2

(12) United States Patent
Bae et al.

(10) Patent No.: US 12,714,694 B2
(45) Date of Patent: Aug. 25, 2026

(54) THIOHYDANTOIN DERIVATIVES AND USES THEREOF

(71) Applicant: CELROS BIOTECH, Seoul (KR)

(72) Inventors: Yun Soo Bae, Gyeonggi-do (KR); Da Un Jeong, Seoul (KR)

(73) Assignee: Celros Biotech, Seoul (KR)

( * ) Notice: Subject to any disclaimer, the term of this patent is extended or adjusted under 35 U.S.C. 154(b) by 767 days.

(21) Appl. No.: 18/043,408

(22) PCT Filed: Aug. 27, 2021

(86) PCT No.: PCT/KR2021/011535
§ 371 (c)(1),
(2) Date: Feb. 28, 2023

(87) PCT Pub. No.: WO2022/045836
PCT Pub. Date: Mar. 3, 2022

(65) Prior Publication Data

US 2023/0330067 A1 Oct. 19, 2023

(30) Foreign Application Priority Data

Aug. 28, 2020 (KR) ........................ 10-2020-0109702
Aug. 28, 2020 (KR) ........................ 10-2020-0109703

(51) Int. Cl.
*A61K 31/4166* (2006.01)
*A61P 25/16* (2006.01)

(52) U.S. Cl.
CPC .......... *A61K 31/4166* (2013.01); *A61P 25/16* (2018.01)

(58) Field of Classification Search
CPC ........................... A61K 31/4166; A61P 25/16
See application file for complete search history.

(56) References Cited

U.S. PATENT DOCUMENTS

| | | | |
|---|---|---|---|
| 5,143,929 | A | 9/1992 | Belliotti et al. |
| 2015/0290208 | A1 | 10/2015 | Page et al. |

FOREIGN PATENT DOCUMENTS

| | | | | |
|---|---|---|---|---|
| CN | 115704026 A | 2/2023 | | |
| KR | 1020010021615 A | 3/2001 | | |
| WO | WO 2007/012670 A2 * | 2/2007 | ........... C07D 233/96 | |
| WO | 2019023448 A1 | 1/2019 | | |

OTHER PUBLICATIONS

Patani, et al., Bioisosterism: A Rational Approach in Drug Design, Chem. Rev. 96, 3147-3176 (1996). (Year: 1996).*
Bae, Y. et al., "Synthesis and biological evaluation of 3-substituted 5-benzylidene-1-methyl-2-thiohydantoins as potent NADPH oxidase (NOX) inhibitors," Bioorganic & Medicinal Chemistry 24 (2016) 4144-4151, Elsevier Ltd.
International Search Report from WIPO mailed Dec. 6, 2021 in Intl. Pat. Appl. No. PCT/KR2021/011535.
Written Opinion of the International Searching Authority from WIPO mailed Dec. 6, 2021 in Intl. Pat. Appl. No. PCT/KR2021/011535.

* cited by examiner

*Primary Examiner* — Erich A Leeser
(74) *Attorney, Agent, or Firm* — Potomac Law Group, PLLC; Judith U. Kim

(57) ABSTRACT

The present invention relates to a thiohydantoin derivative and a composition for preventing or treating NADPH oxidase (NOX)-associated diseases comprising same, and can be used to treat NADPH oxidase (NOX)-associated diseases through excellent actions on NOX inhibition.

18 Claims, 19 Drawing Sheets

B

A

THIOHYDANTOIN DERIVATIVES AND USES THEREOF

TECHNICAL FIELD

The present invention relates to novel thiohydantoin derivatives and uses thereof.

BACKGROUND ART

Parkinson's disease is characterized by neurodegeneration of dopaminergic neurons in the substantia nigra pars compacta (SNc), which causes a gradual depletion of dopamine in the striatum. Parkinson's disease disturbs the balance of basal ganglia circulation and inhibits the proper function of motor neurons, resulting in rigidity, tremor, and akinesia. It is the second most common neurodegenerative disease affecting 1-5% of the population over the age of 50.

The ultimate cause of Parkinson's disease is not yet known, but it is known that various symptoms appear due to a deficiency of dopamine, a neurotransmitter in the brain produced by nerve cells in the substantia nigra area of the midbrain of normal people.

Dopamine produced by nerve cells distributed in the substantia nigra of the brain is connected to the basal ganglia of the brain including the corpus striatum. The basal ganglia is a very important part intricately connected to the motor cortex and other parts of the brain, allowing the human body to perform movements smoothly, harmoniously and accurately. Deficiency of dopamine released from dopaminergic nerve terminals in the basal ganglia as a result of damage to these dopaminergic nerves is a major cause of motor impairment in Parkinson's disease.

There is still no definitive answer to the cause of Parkinson's disease, in other words, what causes the destruction of neurons in the substantia nigra. However, research is being actively conducted to identify the cause of the disease. There are opinions that infection by viral encephalitis, and the like, that immune mechanism is involved, that genetic reasons that the temperament is innately inherited, that free radicals are generated and destroy nerve cells, opinions that there is a problem with the production and metabolism of dopamine, and the like. However, there are still many points that are insufficient to explain Parkinson's disease as a whole.

Meanwhile, 6-hydroxydopamine (6-OHDA) and L-glutamic acid are known as cause substances of Parkinson's disease.

The 6-OHDA is a neurotoxin, and is known to have a chemical structure similar to that of dopamine, be absorbed by the dopamine transporter (DAT), and produce free radicals, which damages dopamine neurons and causes death of nerve cells.

The L-glutamic acid plays a physiologically important role at normal concentrations, but when secreted in excess, the L-glutamic acid acts as an amino acid that causes excitotoxicity, which induces excitotoxicity by excitatory neurotransmitters, resulting in damage or death of nerve cells. As a result, the L-glutamic acid causes not only memory loss and cognitive function decline, but also various neurodegenerative diseases such as Alzheimer's disease, Parkinson's disease, and the like.

Nerve cell damage caused by the excitatory neurotransmitter, neurotoxin, or the like, is caused by excessive nerve cell death in the central nervous system, and thus inhibition of nerve cell death will be very helpful in protecting nerve cells from memory decline, cognitive decline, and furthermore, neurodegenerative diseases.

In particular, recently, in order to protect nerve cells against nerve cell death and degenerative neurological diseases, various drugs such as neurotransmitter receptor antagonists, GABA agonists, intracellular calcium lowering agents, free radical scavengers, and glutamate release inhibitors, and the like, have been attempted to be developed, but most of these drugs have risks and side effects.

In addition, the retina is a transparent and thin membrane located at the innermost part of the eyeball wall and in contact with the vitreous body in the eyeball. The retina acts as a primary visual information organ that converts optical information of objects into electrical signals and transmits images to the central visual area of the brain through the optic nerve. The retina is a sophisticated tissue composed of over 100 million photoreceptor cells, over 1 million ganglion cells, which are visual nerve cells, and numerous nerve cells that act as wires connecting these cells. The macular lutea, which is the central part of the retina that distinguishes colors and objects and represents vision, is composed of a photoreceptor cell layer composed of cone cells and a ganglion cell layer. In the macular lutea, the electrical signal of the image is converted into a chemical signal and transmitted to the brain through the optic nerve, which is the axon of the ganglion cell. The retina other than the macular lutea recognizes the periphery and plays a major role in when it is dark.

When an abnormality occurs in the retina due to aging or external factors, there is a problem with eyesight and sight, and in severe cases, blindness occurs. Retinal diseases include retinal detachment, in which the neuroretina is separated from the retinal pigment epithelium (RPE) cell layer and pulled away from its normal position at the back of your eye, causing visual impairment; peripheral retinal degeneration that causes abnormalities in tissues around the retina; and macular degeneration, in which abnormalities occur in the macular lutea. When the retina is separated from the pigment epithelial layer, it is not possible to receive optical information about images. In addition, since the nutrient supply from the choroid is not achieved, nerve cells fail to function. If nerve cells continue to fail to function, permanent retinal atrophy occurs, resulting in blindness.

The retinal pigment epithelium is located between the neural retina and the choroid and plays an important role in maintaining the function of the retina as a cubic polarized monolayer. Normal retinal pigment epithelium has a morphologically and functionally asymmetrical structure. Deformation of retinal pigment epithelial cells may lead to fibrotic eye diseases such as proliferative vitreoretinopathy (PVR), diabetic retinopathy (DR), and age-related macular degeneration (AMD), and the like. In pathological conditions, retinal pigment epithelial cells are deformed and do not have their own morphology, and lose exocytosis and phagocytosis functions.

Meanwhile, it is important to detect and treat visual impairment early because it cannot be restored to the previous visual acuity once visual impairment begins due to fibrotic transformation of retinal pigment epithelial cells. Fibrotic transformation of retinal pigment epithelial cells may minimize vision loss if detected and treated early, but there is no definitive treatment yet.

The development of various diseases, including the above-mentioned diseases, are associated with NADPH-oxidase.

NADPH oxidases (NOX) are a family of enzymes that have 6 transmembrane domains and transport electrons across biological membranes. These enzymes broadly and specifically modulate redox-sensitive signaling pathways and are associated with various pathogenesis. In general, the electron acceptor is oxygen, and the product of the electron transfer reaction is superoxide. Accordingly, the main biological function of Nox enzymes is the production of reactive oxygen species (ROS) from oxygen. Reactive oxygen species (ROS) are small molecules derived from oxygen, including oxygen radicals (super-oxide anion [$*O_2$], hydroxyl [HO*], peroxyl [ROO], alkoxyl [RO*] and hydroperoxyl [HOO*]), and including other oxidizing agents and/or non-radical compounds that are readily converted to radicals such as hydrogen peroxide ($H_2O_2$).

Various diseases of the central nervous system, including Parkinson's disease, Alzheimer's disease, and the like, commonly show oxidative stress, inflammation, microglia activation, and progressive neuronal cell death in the onset and progression of the disease. It has been reported that the expression of Nox1, Nox2, and Nox4 is increased in the brain of patients with Parkinson's disease, Alzheimer's disease, amyotrophic lateral sclerosis, and the like, and that neuroprotective effects are shown when Nox is knocked out or genetically inactivated in disease-induced experimental animals (Parkinson's animal models by herbicides, LPS, MPP+, and the like, Alzheimer's animal models by APP overexpression, and superoxide dismutase 1 (SOD1) mutant amyotrophic lateral sclerosis animal model).

In addition, dysfunction of retinal pigment epithelial cells caused by oxidative stress is critically involved in the pathogenesis of macular degeneration, and Nox activity is strongly related to dysfunction of vascular endothelial cells and angiogenesis through upregulation of VEGF.

Under the above problems, the present inventors have confirmed that the novel thiohydantoin derivative has an excellent action effect as a Nox inhibitor. In particular, the present inventors completed the present invention by confirming that this Nox inhibitory action is effective in preventing or treating degenerative brain diseases such as Parkinson's disease, retinal diseases such as macular degeneration, and the like.

DISCLOSURE

Technical Problem

An object of the present invention is to provide a novel hydantoin compound, an isomer or a pharmaceutically acceptable salt thereof.

In addition, another object of the present invention is to provide uses of a novel hydantoin compound, an isomer or a pharmaceutically acceptable salt thereof.

Technical Solution

Compound Represented by Chemical Formula 1

In one general aspect, the present invention provides a compound represented by the following Chemical Formula 1, an isomer or a pharmaceutically acceptable salt thereof:

[Chemical Formula 1]

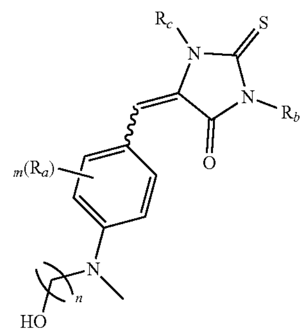

in Chemical Formula 1 above, $R_a$ is hydrogen, a hydroxyl group or a $C_1$-$C_4$ alkoxy group, $R_b$ is a $C_1$-$C_6$ straight chain or branched chain alkyl group, a $C_3$-$C_{10}$ cycloalkyl group, or a —($C_1$-$C_3$ alkyl) $C_6$-$C_{12}$ aryl group, $R_c$ is hydrogen or a $C_1$-$C_4$ alkyl group, n is any integer from 1 to 4, and m is any integer from 1 to 3.

More specifically, the compound represented by Chemical Formula 1 may be a compound represented by the following Chemical Formula 2, an isomer or a pharmaceutically acceptable salt thereof:

[Chemical Formula 2]

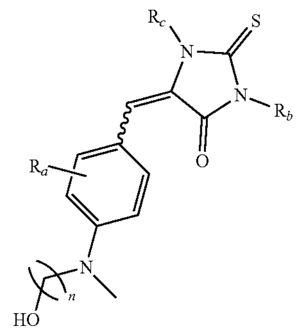

in Chemical Formula 2 above, $R_a$ is hydrogen, a hydroxyl group or a $C_1$-$C_4$ alkoxy group, $R_b$ is a $C_1$-$C_6$ straight chain or branched chain alkyl group, a $C_3$-$C_{10}$ cycloalkyl group, or a —($C_1$-$C_3$ alkyl) $C_6$-$C_{12}$ aryl group, $R_c$ is hydrogen or a $C_1$-$C_4$ alkyl group, and n is any integer from 1 to 4.

More specifically, the compound represented by Chemical Formula 1 may be a compound represented by the following Chemical Formula 3, an isomer or a pharmaceutically acceptable salt thereof:

[Chemical Formula 3]

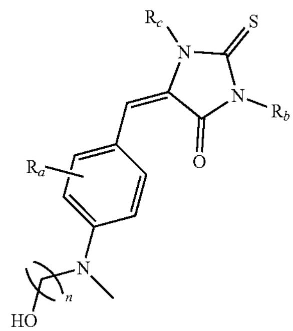

in Chemical Formula 3 above, $R_a$, $R_b$, $R_c$, and n are as defined in Chemical Formula 2 above.

More specifically, the compound represented by Chemical Formula 1 may be a compound represented by the following Chemical Formula 4, an isomer or a pharmaceutically acceptable salt thereof:

[Chemical Formula 4]

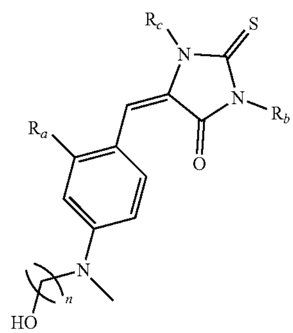

in Chemical Formula 4 above, $R_a$, $R_b$, $R_c$, and n are as defined in Chemical Formula 2 above.

The meanings of terms and symbols used herein are as follows:

As used herein, "alkyl" means a straight-chain or branched-chain monovalent hydrocarbon group of the structure $—C_nH_{(2n+1)}$. Non-limiting examples of the alkyl include methyl, ethyl, propyl, isopropyl, isobutyl, sec-butyl, tert-butyl, pentyl, isopentyl, neopentyl, sec-pentyl, tert-pentyl, hexyl, and the like. For example, "$C_1$-$C_6$alkyl" may refer to a straight-chain or branched-chain alkyl such as methyl, ethyl, propyl, isopropyl, isobutyl, sec-butyl, tert-butyl, pentyl, isopentyl, neopentyl, sec-pentyl, tert-pentyl, or hexyl.

As used herein, "alkoxy" means a functional group containing an alkyl group bonded to an oxygen atom. $C_1$-$C_4$ alkoxy group may refer to alkoxy such as methoxy, ethoxy, propoxy, isopropoxy, n-butoxy or tert-butoxy.

As used herein, "$C_3$-$C_{10}$ cycloalkyl group" means a cyclic, monovalent hydrocarbon group of the structural formula $—C_nH_{(2n-1)}$ containing 3 to 8 carbon atoms. Non-limiting examples of the cycloalkyl group include cyclopropyl, cyclobutyl, cyclopentyl, cyclohexyl, cycloheptyl, cyclooctyl, and the like.

As used herein, "$C_6$-$C_{12}$ aryl" refers to an aromatic hydrocarbon containing 6 or 12 carbon atoms. For example, the aryl may refer to monocyclic (for example, phenyl) or bicyclic (for example, indenyl, naphthalenyl, tetrahydronaphthyl, tetrahydroindenyl) ring system.

As used herein, n is any integer of 1, 2, 3, or 4.

As used herein, m is any integer of 1, 2, or 3.

$R_a$ is hydrogen, a hydroxyl group or a $C_1$-$C_4$ alkoxy group. $R_a$ may preferably be hydrogen, hydroxy, methoxy, or ethoxy.

In the present invention, when $R_b$ is a $C_1$-$C_6$ straight-chain or branched-chain alkyl group, $R_b$ may be, for example, methyl, ethyl, propyl, isopropyl, isobutyl, sec-butyl, tert-butyl, pentyl, isopentyl, neo-pentyl, sec-pentyl, tert-pentyl, hexyl, or the like, but is not limited thereto. $R_b$ may be isobutyl.

When $R_b$ is a $C_3$-$C_{10}$ cycloalkyl group, $R_b$ may preferably be a $C_5$-$C_8$ cycloalkyl group. More specifically, $R_b$ may be cyclopentyl, cyclohexyl, cycloheptyl, or cyclooctyl. $R_b$ may be cyclohexyl.

When $R_b$ is a —($C_1$-$C_3$ alkyl) $C_6$-$C_{12}$ aryl group, preferably, $R_b$ may be benzyl, phenethyl, phenylpropyl, or the like.

$R_c$ may be hydrogen, methyl, ethyl, propyl, isopropyl, isobutyl, sec-butyl or tert-butyl.

In another embodiment, the compound represented by Chemical Formula 1 may be a compound in which in Chemical Formula 1 above, $R_a$ is hydrogen,
$R_b$ is a $C_3$-$C_{10}$ cycloalkyl group,
$R_c$ is a $C_1$-$C_4$ alkyl group,
n is 1 to 4, and
m is 1.

In another embodiment, in the compound represented by Chemical Formula 1 above, $R_a$ is hydrogen,
$R_b$ is a $C_1$-$C_6$ straight chain or branched chain alkyl group,
$R_c$ is a $C_1$-$C_4$ alkyl group,
n is 1 to 4, and
m is 1.

In another embodiment, in the compound represented by Chemical Formula 1 above, in Chemical Formula 1 above, $R_a$ is a hydroxyl group,
$R_b$ is a $C_3$-$C_{10}$ cycloalkyl group,
$R_c$ is a $C_1$-$C_4$ alkyl group,
n is 1 to 4, and
m is 1.

In another embodiment, the compound represented by Chemical Formula 1 may be a compound in which in Chemical Formula 1 above, $R_a$ is a $C_1$-$C_4$ alkoxy group,
$R_b$ is a $C_3$-$C_{10}$ cycloalkyl group,
$R_c$ is a $C_1$-$C_4$ alkyl group,
n is 1 to 4, and
m is 1.

In another embodiment, the compound represented by Chemical Formula 1 may be a compound in which in Chemical Formula 1 above, $R_a$ is hydrogen,
$R_b$ is a —($C_1$-$C_3$ alkyl) $C_6$-$C_{12}$ aryl group,
$R_c$ is a $C_1$-$C_4$ alkyl group,
n is 1 to 4, and
m is 1.

In another embodiment, the compound represented by Chemical Formula 1 may be a compound in which in Chemical Formula 1 above, $R_a$ is a hydroxyl group,
$R_b$ is a —($C_1$-$C_3$ alkyl) $C_6$-$C_{12}$ aryl group,
$R_c$ is a $C_1$-$C_4$ alkyl group,
n is 1 to 4, and
m is 1.

In another embodiment, the compound represented by Chemical Formula 1 may be a compound in which in Chemical Formula 1 above, $R_a$ is a $C_1$-$C_4$ alkoxy group, $R_b$ is a —($C_1$-$C_3$ alkyl) $C_6$-$C_{12}$ aryl group, $R_c$ is a $C_1$-$C_4$ alkyl group, n is 1 to 4, and m is 1.

The compound represented by Chemical Formula 1 may be any one selected from the group consisting of the following compounds:

(E)-3-cyclohexyl-5-(4-((2-hydroxyethyl)(methyl)amino) benzylidene)-1-methyl-2-thioxoimidazolidin-4-one;

(E)-5-(4-((2-hydroxyethyl)(methyl)amino)benzylidene)-3-isobutyl-1-methyl-2-thioxoimidazolidin-4-one;

(Z)-5-(4-((2-hydroxyethyl)(methyl)amino)benzylidene)-3-isobutyl-1-methyl-2-thioxoimidazolidin-4-one;

(E)-3-cyclohexyl-5-(4-((2-hydroxyethyl)(methyl)amino)-2-methoxybenzylidene)-1-methyl-2-thioxoimidazolidin-4-one;

(E)-3-cyclohexyl-5-(2-hydroxy-4-((2-hydroxyethyl) (methyl)amino)benzylidene)-1-methyl-2-thioxoimidazolidin-4-one;

(E)-3-benzyl-5-(4-((3-hydroxypropyl)(methyl)amino)benzylidene)-1-methyl-2-thioxoimidazolidin-4-one;

(E)-3-phenethyl-5-(4-((2-hydroxyethyl)(methyl)amino)benzylidene)-1-methyl-2-thioxoimidazolidin-4-one;

(E)-3-benzyl-5-(2-hydroxy-4-((2-hydroxyethyl)(methyl) amino)benzylidene)-1-methyl-2-thioxoimidazolidin-4-one; and;

(E)-3-benzyl-5-(4-((3-hydroxypropyl)(methyl)amino)-2-methoxybenzylidene)-1-methyl-2-thioxoimidazolidin-4-one.

The compound represented by Chemical Formula 1 of the present invention may contain one or more double bonds, and thus may be present as individual geometric isomers such as cis/trans or (E)/(Z) configuration.

These isomers may be separated by conventional techniques, and for example, the compound represented by Chemical Formula 1 may be separated by column chromatography, HPLC, or the like.

The compound represented by Chemical Formula 1 may be any one selected from the group consisting of the following compounds:

| Example | Structure |
|---|---|
| 1 | 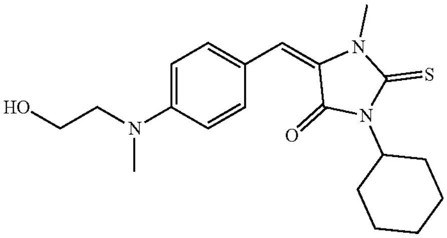 [SMILES: CN1C(=S)N(C2CCCCC2)C(=O)/C1=C\c1ccc(N(C)CCO)cc1] |
| 2 | 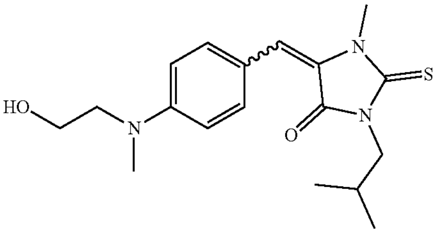 [SMILES: CC(C)CN1C(=O)C(=Cc2ccc(N(C)CCO)cc2)N(C)C1=S] |
| 3 | 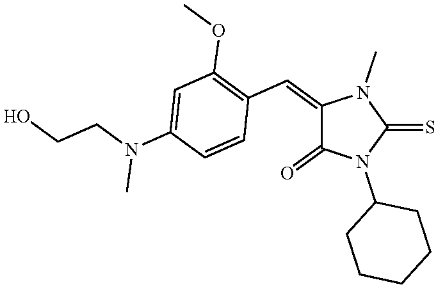 [SMILES: COc1cc(N(C)CCO)ccc1/C=C1\C(=O)N(C2CCCCC2)C(=S)N1C] |

-continued
| Example | Structure |
| --- | --- |
| 4 | 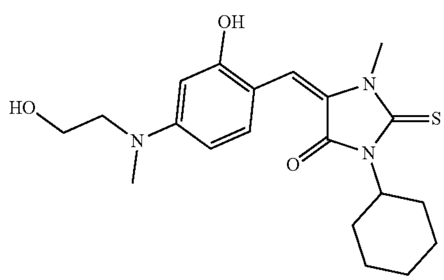 [SMILES: CN1C(=S)N(C2CCCCC2)C(=O)/C1=C\c1ccc(N(C)CCO)cc1O] |
| 5 | 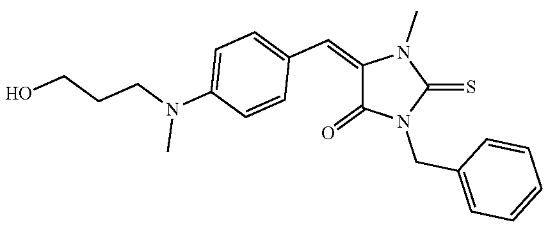 [SMILES: CN1C(=S)N(Cc2ccccc2)C(=O)/C1=C\c1ccc(N(C)CCCO)cc1] |
| 6 | 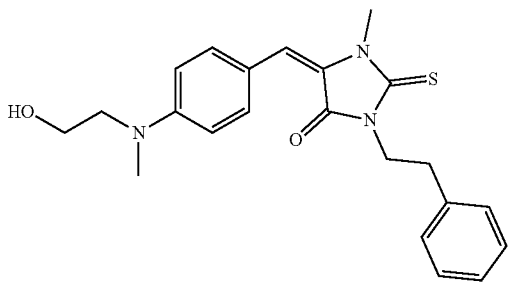 [SMILES: CN1C(=S)N(CCc2ccccc2)C(=O)/C1=C\c1ccc(N(C)CCO)cc1] |
| 7 | 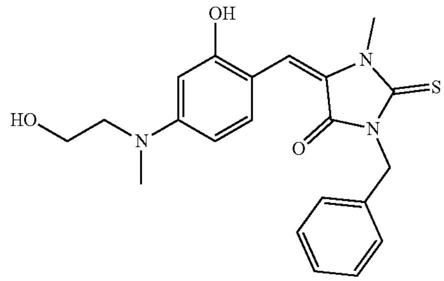 [SMILES: CN1C(=S)N(Cc2ccccc2)C(=O)/C1=C\c1ccc(N(C)CCO)cc1O] |
| 8 | 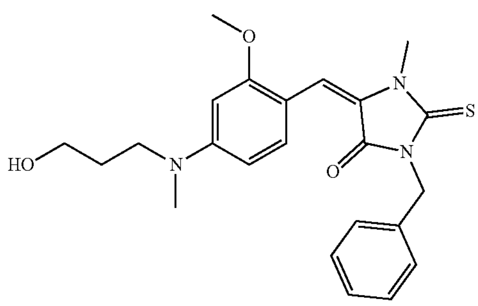 [SMILES: COc1cc(N(C)CCCO)ccc1/C=C1\C(=O)N(Cc2ccccc2)C(=S)N1C] |

The compound of Example 2 may have the following structures according to the (E)/(Z) configuration:

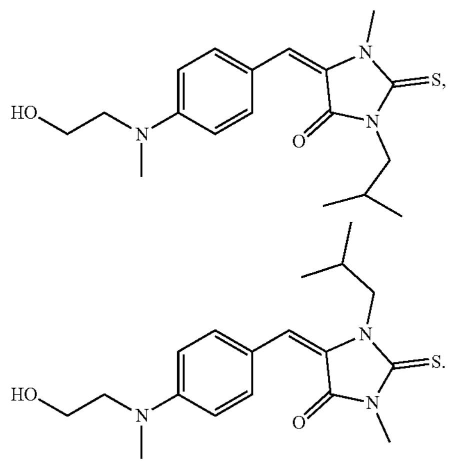

In the present invention, the pharmaceutically acceptable salt means a salt commonly used in the pharmaceutical industry, and may include, for example, inorganic ion salts prepared from calcium, potassium, sodium, magnesium, and the like, inorganic acid salts prepared from hydrochloric acid, nitric acid, phosphoric acid, bromic acid, iodic acid, perchloric acid, and sulfuric acid, and the like; organic acid salts prepared from acetic acid, trifluoroacetic acid, citric acid, maleic acid, succinic acid, oxalic acid, benzoic acid, tartaric acid, fumaric acid, manderic acid, propionic acid, lactic acid, glycolic acid, gluconic acid, galacturonic acid, glutamic acid, glutaric acid, glucuronic acid, aspartic acid, ascorbic acid, carbonic acid, vanillic acid, hydroiodic acid, and the like; sulfonic acid salts prepared from methanesulfonic acid, ethanesulfonic acid, benzenesulfonic acid, p-toluenesulfonic acid, naphthalenesulfonic acid, and the like; amino acid salts prepared from glycine, arginine, lysine, and the like; and amine salts prepared with trimethylamine, triethylamine, ammonia, pyridine, picoline, and the like, but the types of salts referred to in the present invention are not limited by these listed salts.

Use of Compound Represented by Chemical Formula 1

The present invention provides use of a compound represented by the following Chemical Formula 1, an isomer or a pharmaceutically acceptable salt thereof:

[Chemical Formula 1]

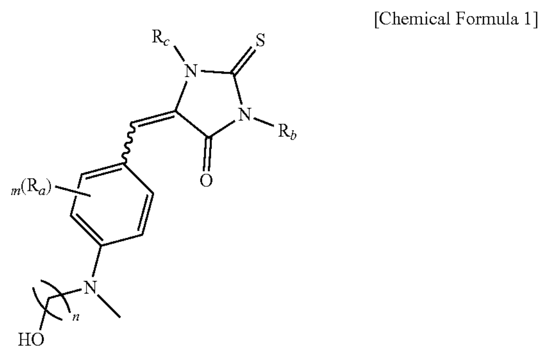

in Chemical Formula 1 above, $R_a$ is hydrogen, a hydroxyl group or a $C_1$-$C_4$ alkoxy group, $R_b$ is a $C_1$-$C_6$ straight chain or branched chain alkyl group, a $C_3$-$C_{10}$ cycloalkyl group, or a —($C_1$-$C_3$ alkyl) $C_6$-$C_{12}$ aryl group, $R_c$ is hydrogen or a $C_1$-$C_4$ alkyl group, n is any integer from 1 to 4, and m is any integer from 1 to 3.

The present invention provides a pharmaceutical composition comprising: the compound represented by Chemical Formula 1, an isomer or a pharmaceutically acceptable salt thereof.

The present invention provides a pharmaceutical composition comprising: the compound represented by Chemical Formula 1, an isomer or a pharmaceutically acceptable salt thereof; and a pharmaceutically acceptable carrier.

The present invention provides a Nox inhibitor comprising: the compound represented by Chemical Formula 1, an isomer or a pharmaceutically acceptable salt thereof.

The compounds according to the present invention may exhibit an excellent effect in inhibiting Nox (NADPH oxidase) and may be used for various therapeutic purposes.

The present invention provides a pharmaceutical composition for preventing or treating NADPH oxidase (NOX)-associated diseases, comprising the compound represented by Chemical Formula 1, an isomer or a pharmaceutically acceptable salt thereof.

Members of the NADPH oxidase (Nox) family are enzymes that generate ROS as a major product. These enzymes generally reduce molecular oxygen in a NADPH-dependent manner to produce superoxide anions. Since the regulatory mechanism of active oxygen production through the control of activity of Nox ultimately has a close relationship with the overall cell signaling system, it is highly related to the treatment for the onset of various diseases as well as the overall cell signaling system.

For example, various diseases of the central nervous system associated with degenerative brain diseases, including Parkinson's disease, Alzheimer's disease, and the like, commonly show oxidative stress and neuroinflammation in the onset and progression of the disease. In particular, Nox is identified as an upstream factor regulating both oxidative stress and neuroinflammation. Therefore, inactivation or pharmacological inhibition of Nox may be expected to have a strong neuroprotective effect (for example, dopaminergic neuron protection, improvement of microglia pathology, and the like) and a behavioral improvement effect in a wide range of neurological diseases.

For example, dysfunction of retinal pigment epithelial cells may occur due to oxidative stress, and these functional disorders are critically involved in the pathogenesis of retinal diseases, and the activity of Nox is strongly related to dysfunction of vascular endothelial cells and angiogenesis through upregulation of VEGF. Thus, inhibition of Nox is able to exhibit excellent effects in the treatment of diseases.

For example, Nox inhibitors may have anti-tumor effects, restore sensitivity to immunotherapy, and/or improve responsiveness to immunotherapy. In addition, the Nox inhibitors may exhibit an inhibitory effect on choroidal neovascularization. In addition, it is possible to inhibit expression of inflammatory factors, and the like.

Accordingly, examples of the NADPH oxidase (NOX)-associated disease may include psoriasis, rheumatoid arthritis, osteoarthritis, restenosis, atherosclerosis, ulcers, liver cirrhosis, glomerulonephritis, diabetic nephropathy, malignant nephrosclerosis, thrombotic microangiopathy, organ transplant rejection, diabetes, hypertension, cardiac hypertrophy, heart failure, restenosis, cancer, autoimmune diseases, inflammatory diseases, degenerative brain diseases, retinal diseases, and the like.

The autoimmune disease includes alopecia areata, ankylosing spondylitis, antiphospholipid syndrome, autoimmune diseases of the adrenal gland, autoimmune hemolytic anemia, autoimmune hepatitis, autoimmune oophoritis, autoimmune orchitis, autoimmune thrombocytopenia, Behçet's disease, bullous pemphigoid, cardiomyopathy, chronic fatigue immune dysfunction syndrome, chronic inflammatory demyelinating polyneuropathy, scarring pemphigoid, CREST syndrome, cold agglutinin disease, Crohn's disease, discoid lupus, Graves' disease, Guillain-Barre syndrome, Hashimoto's thyroiditis, idiopathic pulmonary fibrosis, idiopathic thrombocytopenic purpura, IgA neuritis, juvenile arthritis, lichen planus, lupus erythematosus, Meniere's disease, mixed connective tissue disease, multiple sclerosis, type I or immune-mediated diabetes, myasthenia gravis, pemphigus vulgaris, pernicious anemia, polyarteritis crystals, polychondritis, autoimmune polyglandular syndrome, polymyalgia rheumatica, polymyositis and dermatomyositis, primary agammaglobulinemia, primary biliary cirrhosis, systemic lupus erythematosus, lupus erythematosus, Takayasu's arteritis, temporal arteritis, giant cell arteritis, ulcerative colitis, uveitis, vitiligo, and Wegener's granulomatosis, but is not limited thereto.

Examples of inflammatory diseases capable of being prevented or treated by the composition of the present invention include asthma, encephalitis, inflammatory enteritis, chronic obstructive pulmonary disease, allergy, septic shock, pulmonary fibrosis, undifferentiated spondyloarthropathy, undifferentiated arthropathy, arthritis, inflammatory osteolysis, and chronic inflammation due to chronic viral or bacterial infection, but the inflammatory disease is not limited thereto.

According to a preferred embodiment of the present invention, examples of cancers capable of being prevented or treated by the composition of the present invention include brain cancer, neuroendocrine cancer, gastric cancer, lung cancer, breast cancer, ovarian cancer, liver cancer, bronchial cancer, nasopharyngeal cancer, laryngeal cancer, pancreatic cancer, bladder cancer, adrenal cancer, colorectal cancer, colon cancer, cervical cancer, prostate cancer, bone cancer, skin cancer, thyroid cancer, parathyroid cancer and ureter cancer, but the cancer is not limited thereto.

More specifically, the compound represented by Chemical Formula 1 according to the present invention, an isomer or a pharmaceutically acceptable salt thereof is useful for preventing or treating degenerative brain diseases.

Accordingly, the present invention provides a pharmaceutical composition for preventing or treating degenerative brain diseases, comprising the compound represented by Chemical Formula 1, an isomer or a pharmaceutically acceptable salt thereof.

Non-limiting examples of degenerative brain diseases in the present invention include Parkinson's disease, Huntington's disease, Alzheimer's disease, mild cognitive impairment, senile dementia, amyotrophic lateral sclerosis, spinocerebellar atrophy, Tourette's syndrome, Friedrich's ataxia, Machado-Joseph's disease, Lewy body dementia, dystonia, progressive supranuclear palsy, frontotemporal dementia, and the like.

More specifically, the compound represented by Chemical Formula 1 according to the present invention, an isomer or a pharmaceutically acceptable salt thereof is useful for preventing or treating retinal diseases.

Accordingly, the present invention provides a pharmaceutical composition for preventing or treating retinal diseases, comprising the compound represented by Chemical Formula 1, an isomer or a pharmaceutically acceptable salt thereof.

Non-limiting examples of retinal diseases in the present invention may include glaucoma, retinopathy of prematurity, proliferative retinopathy, corneal transplant rejection, proliferative vitreoretinopathy, diabetic retinopathy, macular degeneration, choroidal neovascularization, retinal edema, and the like. Specifically, the macular degeneration may be wet macular degeneration or dry macular degeneration.

In addition, in view of drug delivery, the pharmaceutical composition may exhibit excellent efficacy in passing through the blood-brain barrier (BBB).

For administration, the pharmaceutical composition of the present invention may further comprise at least one pharmaceutically acceptable carrier in addition to the compound represented by Chemical Formula 1, an isomer or a pharmaceutically acceptable salt thereof. The pharmaceutically acceptable carrier may be saline, sterile water, Ringer's solution, buffered saline, dextrose solution, maltodextrin solution, glycerol, ethanol, or a mixture of one or more of these components, and, if necessary, may contain other conventional additives such as antioxidants, buffers, bacteriostatic agents, and the like. Further, diluents, dispersants, surfactants, binders and lubricants may be additionally added and may be formulated into injectable formulations such as aqueous solutions, suspensions, emulsions, and the like, pills, capsules, granules or tablets. Accordingly, the pharmaceutical composition of the present invention may be a patch, liquid, pill, capsule, granule, tablet, suppository, or the like. These preparations may be prepared by conventional methods used for formulation in the art or a method disclosed in the document [see, Remington's Pharmaceutical Science (latest edition), Mack Publishing Company, Easton PA], and formulated into various preparations depending on each disease or component.

The pharmaceutical composition of the present invention may be administered orally or parenterally (for example, intravenous, subcutaneous, intraperitoneal or topical application) depending on the desired method, and the dosage varies depending on the patient's weight, age, sex, health condition, diet, administration time, administration method, excretion rate, type and severity of disease, and the like. The daily dosage of the compound represented by Chemical Formula 1 of the present invention may be about 0.01 to 1000 mg/kg, preferably 0.1 to 100 mg/kg, and the compound represented by Chemical Formula 1 of the present invention may be administered in an amount divided into one to several times a day.

In other words, the composition may be administered through any general route as long as the composition is able to reach the target tissue, but for example, the composition may be administered through intradermal injection, intravein injection, intraperitoneal injection, intravitreal injection, subcutaneous injection using an osmotic pump, or the like.

The pharmaceutical composition of the present invention may further comprise at least one active ingredient exhibiting the same or similar efficacy in addition to the compound represented by Chemical Formula 1, an isomer or a pharmaceutically acceptable salt thereof.

The present invention provides a method for treating or preventing NADPH oxidase (NOX)-associated diseases, comprising: administering, to a subject in need thereof, a therapeutically effective amount of the compound represented by Chemical Formula 1, an isomer or a pharmaceutically acceptable salt thereof.

The present invention provides a method for treating or preventing degenerative brain diseases, comprising: administering, to a subject in need thereof, a therapeutically effective amount of the compound represented by Chemical Formula 1, an isomer or a pharmaceutically acceptable salt thereof.

The present invention provides a method for treating or preventing retinal diseases, comprising: administering, to a subject in need thereof, a therapeutically effective amount of the compound represented by Chemical Formula 1, an isomer or a pharmaceutically acceptable salt thereof.

The term "therapeutically effective amount" as used herein refers to an amount of the compound represented by Chemical Formula 1, an isomer or a pharmaceutically acceptable salt effective for preventing or treating the diseases.

The treatment method of the present invention includes not only treating the disease itself prior to the onset of symptoms, but also inhibiting or avoiding symptoms thereof, by administering the compound represented by Chemical Formula 1. In the management of diseases, a prophylactic or therapeutic dose of a particular active ingredient will vary depending on the nature and severity of the disease or condition and the route by which the active ingredient is administered. The dose and frequency of dose will vary depending on the individual patient's age, weight and response. A suitable dosage regimen may be readily selected by those skilled in the art who take these factors for granted. In addition, the treatment method of the present invention may further comprise administration of a therapeutically effective amount of an additional active agent useful for the treatment of diseases together with the compound represented by Chemical Formula 1, wherein the additional active agent may exhibit synergistic or auxiliary effects together with the compound represented by Chemical Formula 1.

The present invention provides a food composition for preventing or improving NADPH oxidase (NOX)-associated diseases, comprising the compound represented by Chemical Formula 1, an isomer or a pharmaceutically acceptable salt thereof.

The present invention provides a food composition for preventing or improving degenerative brain diseases, comprising the compound represented by Chemical Formula 1, an isomer or a pharmaceutically acceptable salt thereof.

The present invention provides a food composition for preventing or improving retinal diseases, comprising the compound represented by Chemical Formula 1, an isomer or a pharmaceutically acceptable salt thereof.

The food composition of the present invention may be used as a health functional food. The term "health functional food" refers to food manufactured and processed using raw materials or ingredients having useful functionality for human body in accordance with Health Functional Food Act No. 6727, wherein the term "functional" means intake for the purpose of obtaining useful effects for health purposes, such as adjusting nutrients or physiological functions for the structure and function of the human body.

The food composition of the present invention may comprise conventional food additives, and the suitability of the "food additives" is judged by specifications and standards for relevant items in accordance with general test methods and general principles of Korean Food Additives Code approved by the Food and Drug Administration, unless there is no other regulation thereto.

For the purpose of preventing and/or improving the diseases, the food composition of the present invention may contain the compound represented by Chemical Formula 1 in an amount of 0.01 to 95 wt %, preferably 1 to 80 wt %, based on the total weight of the composition. Further, for the purpose of preventing and/or improving the above diseases, the food composition of the present invention may be manufactured and processed in the form of tablets, capsules, powders, granules, liquids, pills, beverages, and the like.

In addition, the present invention provides use of the compound represented by Chemical Formula 1, an isomer or a pharmaceutically acceptable salt thereof for the manufacture of medicaments for the treatment of NADPH oxidase (NOX)-associated diseases.

Further, the present invention provides use of the compound represented by Chemical Formula 1, an isomer or a pharmaceutically acceptable salt thereof for the manufacture of medicaments for the treatment of degenerative brain diseases.

Further, the present invention provides use of the compound represented by Chemical Formula 1, an isomer or a pharmaceutically acceptable salt thereof for the manufacture of medicaments for the treatment of retinal diseases.

The compound represented by Chemical Formula 1 for the manufacture of medicaments may be mixed with acceptable adjuvants, diluents, carriers, and the like, and may be prepared as a combined preparation with other active agents to have a synergistic effect of the active ingredients.

Further, the present invention provides a food composition for enhancing cognitive function comprising the compound represented by Chemical Formula 1, an isomer or a pharmaceutically acceptable salt thereof.

The present invention also includes the following embodiments:

a compound represented by Chemical Formula 1 as defined in any of the embodiments described herein, an isomer or a pharmaceutically acceptable salt thereof, for use as a medicament;

a compound represented by Chemical Formula 1 as defined in any of the embodiments described herein, an isomer or a pharmaceutically acceptable salt thereof, for use in the prevention or treatment of the diseases discussed herein;

a method for treating the above-described diseases comprising administering, to a subject in need thereof, a therapeutically effective amount of the compound represented by Chemical Formula 1 as defined in any of the embodiments described herein, an isomer or a pharmaceutically acceptable salt thereof;

a compound represented by Chemical Formula 1 as defined in any of the embodiments described herein, an isomer or a pharmaceutically acceptable salt thereof, for the manufacture of medicaments for the treatment of the above-described diseases;

a Nox inhibitor comprising a compound represented by Chemical Formula 1 as defined in any of the embodiments described herein, an isomer or a pharmaceutically acceptable salt thereof; and an antioxidant comprising a compound represented by Chemical Formula 1 as defined in any of the embodiments described herein, an isomer or a pharmaceutically acceptable salt thereof.

All examples, isomers thereof, or pharmaceutically acceptable salts thereof may be claimed individually or as a group together in any combination with any number of each and every embodiment described herein.

Matters described in the composition, use, and treatment method of the present invention are equally applied unless they contradict each other.

Advantageous Effects

The compound represented by Chemical Formula 1 according to the present invention, an isomer or a pharmaceutically acceptable salt thereof exhibits excellent Nox inhibitory effect. In particular, the compound represented by Chemical Formula 1 according to the present invention, an isomer or a pharmaceutically acceptable salt thereof exhibits excellent effects in the treatment of NADPH oxidase (NOX)-associated diseases, comprising degenerative brain diseases, retinal diseases, and the like.

BEST MODE

Figure 1:
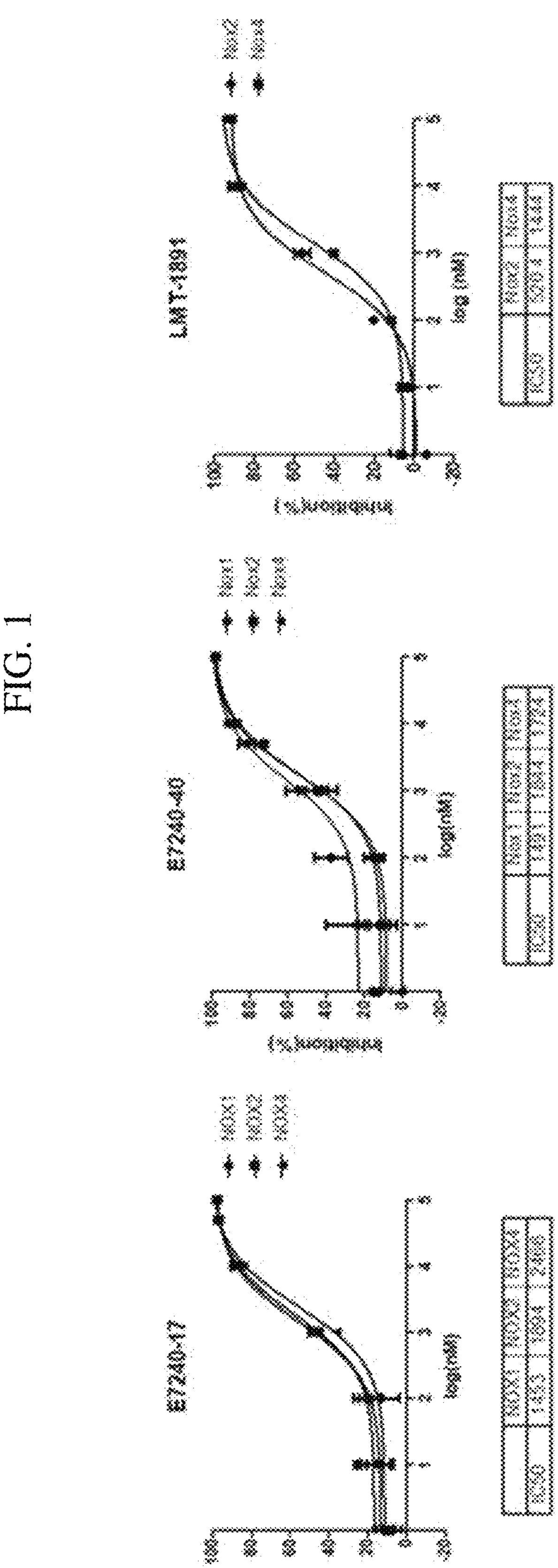
FIG. 1 shows $IC_{50}$ value measurement results of compounds according to the present invention for confirming the Nox inhibitory effect.

Hereinafter, embodiments of the present invention will be described in detail so that those skilled in the art are able to easily practice the present invention. However, the present invention may be implemented in various different forms and is not limited to the embodiments described herein.

Reagents and solvents described below were purchased from Sigma-Aldrich and TCI unless otherwise specified.

$^1H$- and $^{13}C$-NMR of all compounds were measured with a Bruker AV-500, and $CDCl_3$ ($d_H$=7.26 ppm and $d_C$=77.0 ppm) was employed as an internal standard. NMR data were obtained using MNova 10.0 processing software (Mestrelab Research).

High-resolution mass spectrometry was performed using a Joel JMS-700 mass spectrometer based on electrical ionization.

Example 1. Synthesis of (E)-3-cyclohexyl-5-(4-((2-hydroxyethyl)(methyl)amino)benzylidene)-1-methyl-2-thioxoimidazolidin-4-one (E7240-17)

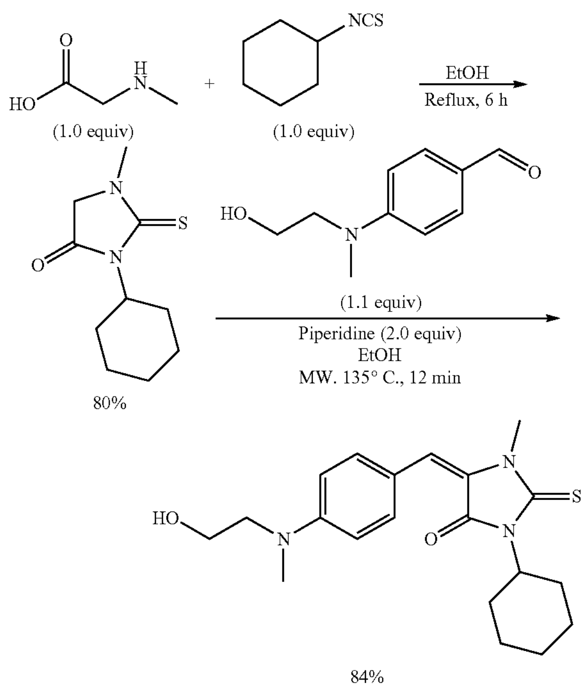

Synthesis of 3-cyclohexyl-1-methyl-2-thioxoimidazolidin-4-one (8.51 g, 80% yield, white solid)

Cyclohexyl isothiocyanate (7.77 g, 55.0 mmol) was added to a stirred solution of sarcosine (4.45 g, 50.0 mmol) in absolute ethanol (50 mL). The reaction mixture was refluxed for 6 hours and then cooled to room temperature. The precipitated solid was filtered, washed with ethanol (10 mL) and dried to obtain the corresponding thiohydantoin.

$^1$H NMR (500 MHz, $CDCl_3$): $\delta_H$ 4.52 (tt, J=12.4, 3.9 Hz, 1H), 3.95 (s, 2H), 3.33 (s, 3H), 2.22 (qd, J=12.6, 3.7 Hz, 2H), 1.85 (dt, J=13.5, 3.3 Hz, 2H), 1.76-1.63 (m, 3H), 1.37 (qt, J=13.2, 3.5 Hz, 2H), 1.24 (qt, J=13.0, 3.4 Hz, 1H) ppm.

Synthesis of (E)-3-cyclohexyl-5-(4-((2-hydroxyethyl)(methyl)amino)benzylidene)-1-methyl-2-thioxoimidazolidin-4-one (3.14 g, 84% yield, orange solid)

To a Teflon-sealed glass bottle (20 mL capacity), 3-cyclohexyl-1-methyl-2-thioxoimidazolidin-4-one (2.12 g, 10.0 mmol), N-methyl-N-(2-hydroxyethyl)-4-aminobenzaldehyde (1.97 g, 11.0 mmol), piperidine (1.70 g, 20.0 mmol), and ethanol (10 mL) were added, and then placed in a microwave cavity at 135° C. and 3.50-5.00 Bar for 12 minutes at 60 Watts. The reaction mixture was allowed to reach room temperature. The resulting solid was filtered, washed with ethanol (10 mL), and dried to obtain the product.

$^1$H NMR (500 MHz, DMSO-$d_6$): $\delta_H$ 8.15 (d, J=9.1 Hz, 2H), 6.80 (s, 1H), 6.77-6.72 (m, 2H), 4.75 (bs, 1H), 4.67-4.57 (m, 1H), 3.57 (m, 5H), 3.50 (t, J=6.0 Hz, 2H), 3.04 (s, 3H), 2.27 (q, J=12.4 Hz, 2H), 1.82 (d, J=12.9 Hz, 2H), 1.71-1.56 (m, 3H), 1.36-1.23 (m, 2H), 1.23-1.12 (m, 1H) ppm; $^{13}$C NMR (125 MHz, DMSO-$d_6$): $\delta_C$ 173.9, 161.6, 151.0, 134.0, 124.9, 124.3, 120.0, 111.4, 58.7, 55.2, 54.3, 31.6, 28.7, 26.1, 25.4 ppm; HRMS (EI) m/z $[M]^+$ calcd for $C_{20}H_{27}N_3O_2S$, 373.1824, found 373.1824.

Example 2. Synthesis of 5-(4-((2-hydroxyethyl)(methyl)amino)benzylidene)-3-isobutyl-1-methyl-2-thioxoimidazolidin-4-one (E7240-40)

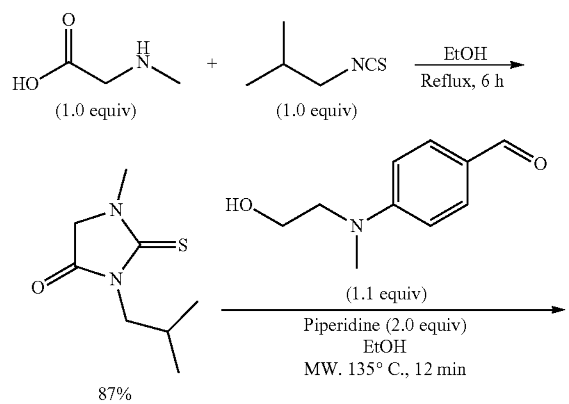

-continued

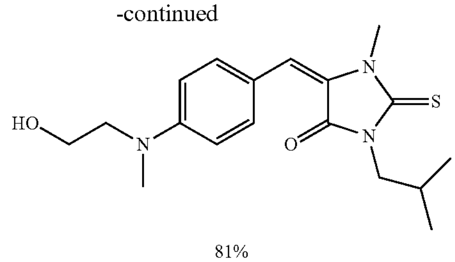

(1) Synthesis of 3-isobutyl-1-methyl-2-thioxoimidazolidin-4-one (4.07 g, 87% yield, brown solid)

Isobutyl isothiocyanate (3.17 g, 27.5 mmol) was added to a stirred solution of sarcosine (2.23 g, 25.0 mmol) in absolute ethanol (25 mL). The reaction mixture was refluxed for 6 hours and then cooled to room temperature. The precipitated solid was filtered, washed with ethanol (10 mL) and dried to obtain the corresponding thiohydantoin.

$^1$H NMR (500 MHz, $CDCl_3$): δ 4.04 (d, J=0.6 Hz, 2H), 3.64 (d, J=7.5 Hz, 2H), 3.35 (s, 3H), 2.35-2.16 (m, 1H), 0.93 (d, J=6.7 Hz, 6H) ppm.

(2) Synthesis of 5-(4-((2-hydroxyethyl)(methyl)amino)benzylidene)-3-isobutyl-1-methyl-2-thioxoimidazolidin-4-one (2.81 g, 81% yield, orange solid)

To a Teflon-sealed glass bottle (20 mL capacity), 3-isobutyl-1-methyl-2-thioxoimidazolidin-4-one (1.86 g, 10.0 mmol), N-methyl-N-(2-hydroxyethyl)-4-aminobenzaldehyde (1.97 g, 11.0 mmol), piperidine (1.70 g, 20.0 mmol), and ethanol (10 mL) were added, and then placed in a microwave cavity at 135° C. and 3.50-5.00 Bar for 12 minutes at 60 Watts. The reaction mixture was allowed to reach room temperature. The resulting solid was filtered, washed with ethanol (10 mL), and dried to obtain the product as a mixture of E/Z isomers in a 1:1.25 ratio.

$^1$H NMR (500 MHz, $CDCl_3$): $\delta_H$ 8.12 (d, J=9.0 Hz, 2H), 7.29 (d, J=8.9 Hz, 5H), 6.93 (s, 1H), 6.83-6.74 (m, 4H), 6.47 (s, 1H), 3.89 (s, 4H), 3.78 (dd, J=9.9, 7.5 Hz, 4H), 3.65 (s, 3H), 3.61 (dt, J=11.1, 5.7 Hz, 4H), 3.49 (s, 3H), 3.10 (d, J=11.9 Hz, 5H), 2.34 (dt, J=14.3, 7.1 Hz, 2H), 0.97 (dd, J=6.7, 4.3 Hz, 11H) ppm.

Example 3. Synthesis of (E)-3-cyclohexyl-5-(4-((2-hydroxyethyl)(methyl)amino)-2-methoxybenzylidene)-1-methyl-2-thioxoimidazolidin-4-one (LMT-1890)

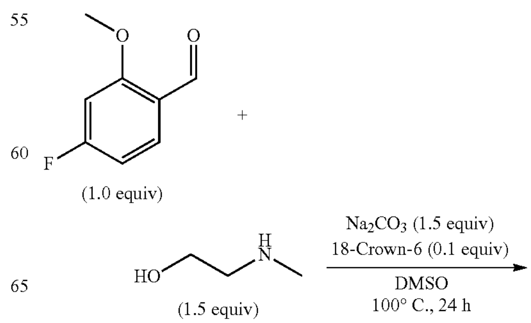

-continued

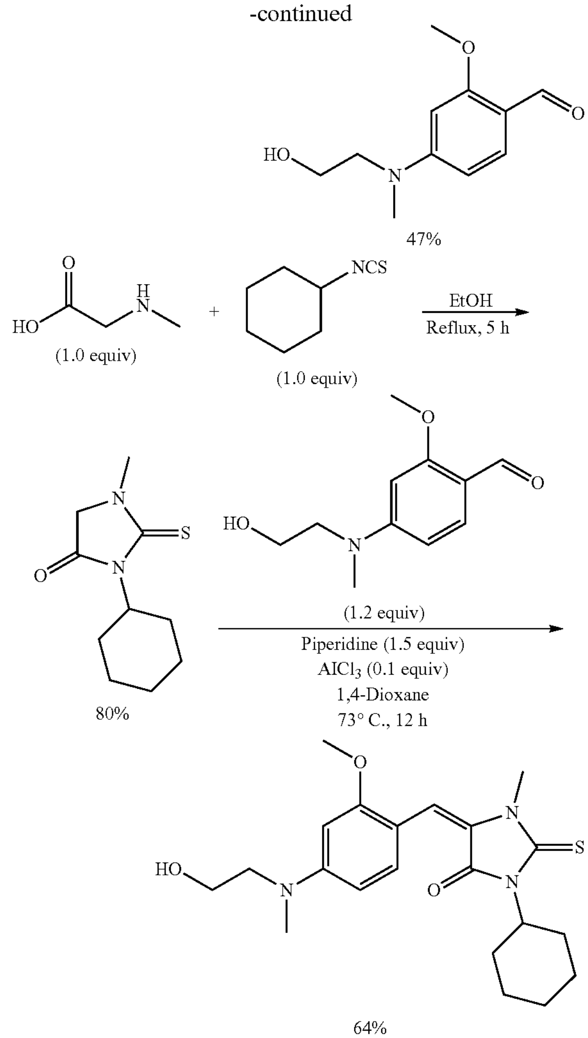

(1) Synthesis of 4-((2-hydroxyethyl)(methyl) amino)-2-methoxybenzaldehyde (318 mg, 47% yield, white solid)

To a solution of 2-(methylamino)ethanol (0.4 mL, 4.9 mmol) and $Na_2CO_3$ (515 mg, 4.9 mmol) in DMSO (20 mL), 4-fluoro-2-substituted benzaldehyde (500 mg, 3.2 mmol) and 18-crown-6 (86 mg, 0.3 mmol) were added. The reaction mixture was stirred at 100° C. for 24 hours. The mixture was extracted with ethyl acetate (10 mL) (×3). The combined organic layers were dried over anhydrous $MgSO_4$, filtered and concentrated in vacuo. The residue was purified by filtration and silica chromatography to obtain the product.

$^1$H NMR (500 MHz, DMSO-$d_6$): $\delta_H$ 10.00 (s, 1H), 7.50 (d, J=8.85 Hz, 1H), 6.39 (dd, J=9.00, 1.68 Hz, 1H), 6.21 (d, J=2.14 Hz, 1H), 4.79 (t, J=5.34 Hz, 1H), 3.87 (s, 3H), 3.58 (q, J=5.39 Hz, 2H), 3.55-3.48 (m, 2H), 3.07 (s, 3H) ppm.

(2) Synthesis of (E)-3-cyclohexyl-5-(4-((2-hydroxyethyl)(methyl)amino)-2-methoxybenzylidene)-1-methyl-2-thioxoimidazolidin-4-one (153 mg, 64% yield, orange solid)

To a stirred solution of 3-cyclohexyl-1-methyl-2-thioxoimidazolidin-4-one (127 mg, 0.6 mmol), 4-((2-hydroxyethyl)(methyl)amino)-2-methoxybenzaldehyde (150 mg, 0.7) and piperidine (0.08 mL, 0.9 mmol) in 1,4-dioxane (5 mL), $AlCl_3$ (8 mg, 0.1 mmol) was added. The stirred reaction mixture was heated to 68-80° C. until the reaction was completed. The mixture was then extracted with ethyl acetate (10 mL) (×3). The combined organic layers were dried over anhydrous $MgSO_4$, filtered and concentrated in vacuo. The residue was purified by filtration and silica chromatography to obtain the product.

$^1$H NMR (500 MHz, $CDCl_3$): $\delta_H$ 8.56 (d, J=8.80 Hz, 1H), 6.96 (s, 1H), 6.46-6.36 (m, 1H), 6.20 (d, J=2.45 Hz, 1H), 4.77-4.66 (m, 1H), 3.92-3.83 (m, 5H), 3.67-3.52 (m, 5H), 3.13-3.02 (m, 3H), 2.43-2.26 (m, 2H), 1.83 (d, J=12.72 Hz, 2H), 1.55-1.77 (m, 6H), 1.36 (q, J=13.21 Hz, 2H), 1.25 (t, J=12.96 Hz, 1H) ppm; $^{13}$C NMR (125 MHz, $CDCl_3$): $\delta_C$ 174.9, 161.9, 159.9, 152.9, 132.5, 125.6, 116.7, 109.8, 104.2, 94.0, 60.4, 55.5, 54.6, 39.1, 35.3, 31.3, 28.6, 26.0, 25.2 ppm; HRMS (EI) m/z $[M]^+$ calcd for $C_{21}H_{29}N_3O_3S$, 402.1, found 402.3.

Example 4. Synthesis of (E)-3-cyclohexyl-5-(2-hydroxy-4-((2-hydroxyethyl)(methyl)amino)benzylidene)-1-methyl-2-thioxoimidazolidin-4-one (15 mg, 52% yield, orange solid) (LMT-1891)

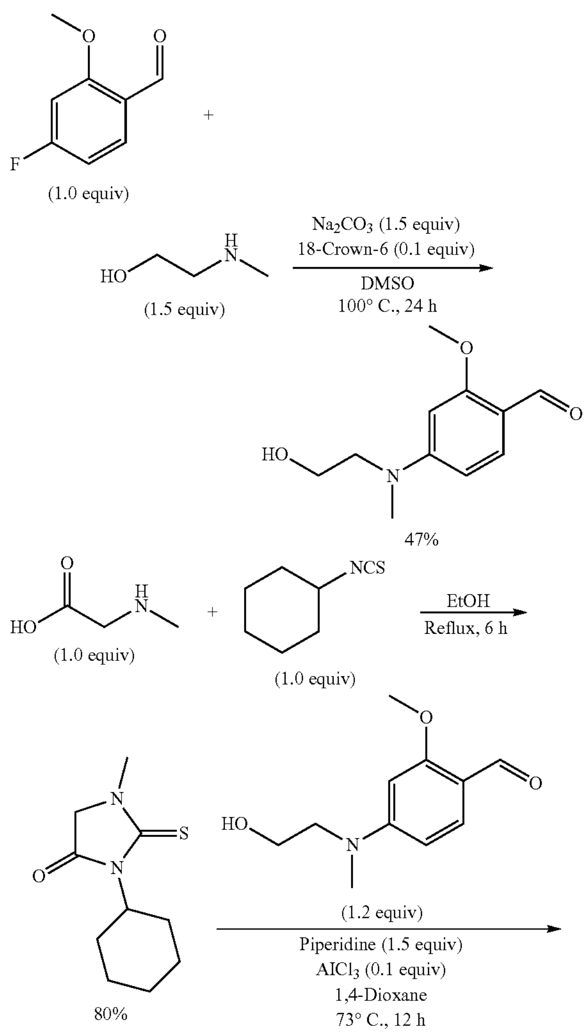

-continued

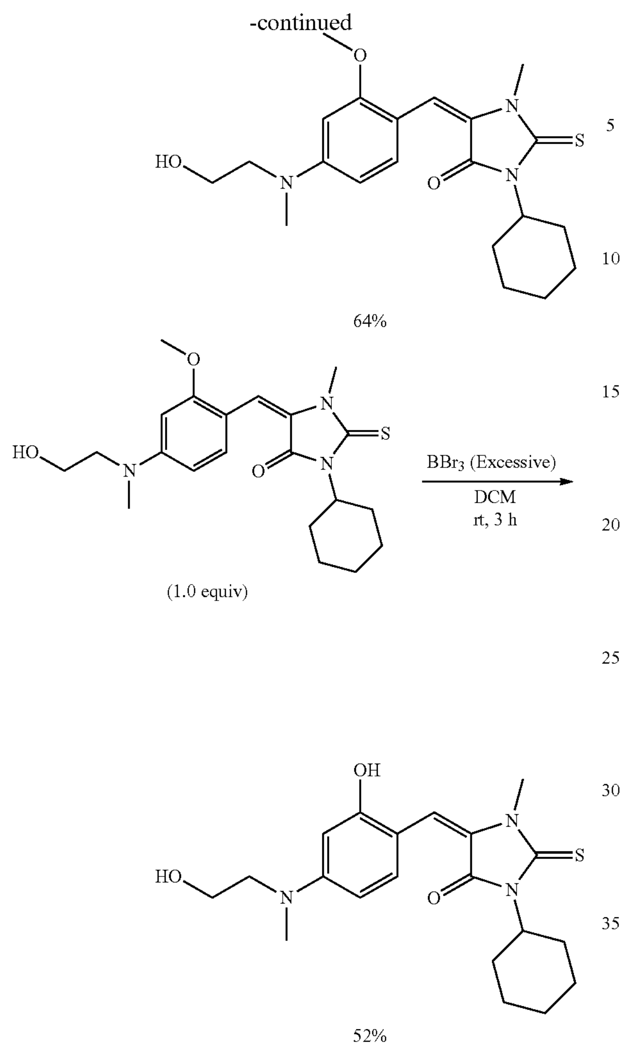

The compound of Example 3 was then used. A solution of (E)-3-cyclohexyl-5-(4-((2-hydroxyethyl)(methyl)amino)-2-methoxybenzylidene)-1-methyl-2-thioxoimidazolidin-4-one in anhydrous dichloromethane was cooled in a dry ice/acetone bath under a nitrogen atmosphere. $BBr_3$ (0.05 mL, 0.6 mmol) was added dropwise. The cooling bath was removed and the reaction mixture was stirred at room temperature for 3 hours. The mixture was cooled on an ice bath and excess $BBr_3$ was quenched by dropwise addition of methanol. The resulting solution was stirred at room temperature for 2 hours. After removing the solvent, the residue was treated with $H_2O$ (10 mL) and ethyl acetate (10 mL). The combined organic layers were washed with $H_2O$, dried over $Na_2SO_4$ and concentrated. The residue was purified by silica chromatography to obtain the product of Example 3.

$^1$H NMR (500 MHz, $CDCl_3$): $\delta_H$ 8.64 (d, J=9.29 Hz, 1H), 7.14 (s, 1H), 6.31 (dd, J=9.29, 2.45 Hz, 1H), 6.17 (d, J=2.45 Hz, 1H), 4.74 (bs, 1H), 3.78-3.66 (m, 2H), 3.58 (s, 2H), 3.55-3.46 (m, 2H), 3.43 (s, 1H), 3.09-2.99 (m, 3H), 2.44-2.24 (m, 2H), 1.87 (d, J=13.21, 2H), 1.69 (t, J=11.74 Hz, 3H), 1.37 (q, J=12.88 Hz, 2H), 1.31-1.17 (m, 2H) ppm; $^{13}$C NMR (125 MHz, $CDCl_3$): $\delta_C$ 171.4, 164.4, 158.7, 136.7, 132.2, 120.6, 113.3, 109.7, 106.5, 102.9, 60.3, 54.3, 39.1, 31.6, 28.6, 25.9, 25.1 ppm; HRMS (EI) m/z $[M]^+$ calcd for $C_{20}H_{27}N_3O_3S$, 388.1, found 388.3.

Example 5. Synthesis of (E)-3-benzyl-5-(4-((3-hydroxypropyl)(methyl)amino)benzylidene)-1-methyl-2-thioxoimidazolidin-4-one (LMT-1889)

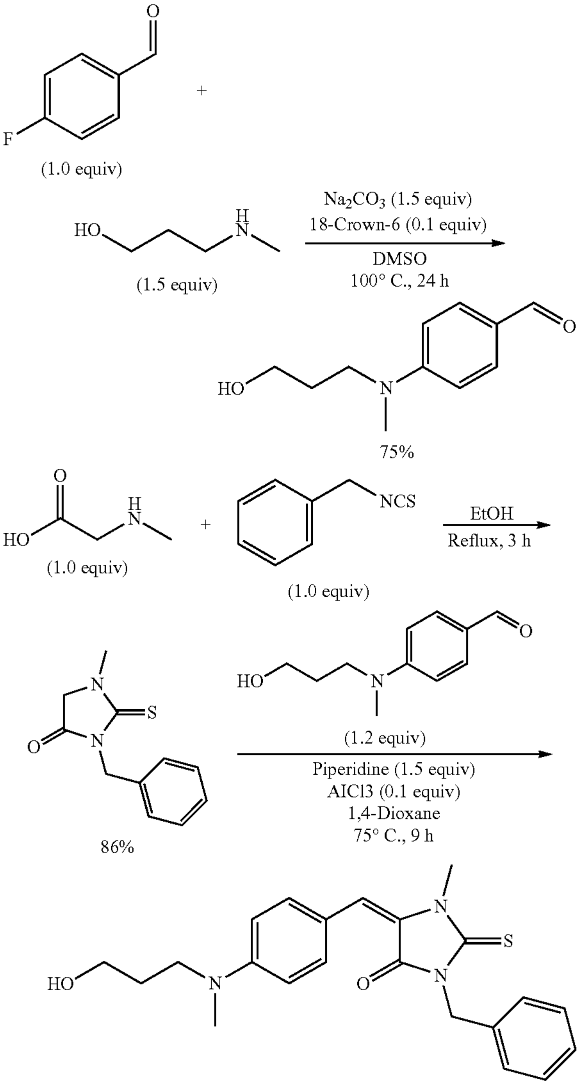

(1) Synthesis of 4-((3-hydroxypropyl)(methyl)amino)benzaldehyde (870 mg, 75% yield, orange liquid)

To a solution of 3-(methylamino)propanol (0.9 mL, 9.0 mmol) and $Na_2CO_3$ (954 mg, 9.0 mmol) in DMSO (20 mL), 4-fluorobenzaldehyde (500 mg, 6.0 mmol) and 18-crown-6 (158 mg, 0.6 mmol) were added. The reaction mixture was stirred at 100° C. for 24 hours. The mixture was extracted with ethyl acetate (10 mL) (×3). The combined organic layers were dried over anhydrous $MgSO_4$, filtered and concentrated in vacuo. The residue was purified by filtration and silica chromatography to obtain the product.

$^1$H NMR (500 MHz, DMSO-$d_6$): $\delta_H$ 9.65 (s, 1H), 7.76-7.60 (m, 2H), 6.80 (m, J=8.85 Hz, 2H), 4.59 (t, J=5.04 Hz, 1H), 3.50 (t, J=7.32 Hz, 2H), 3.48-3.42 (m, 2H), 3.01 (s, 3H), 1.74-1.64 (m, 2H) ppm.

(2) Synthesis of 3-benzyl-1-methyl-2-thioxoimidazolidin-4-one (1.062 g, 86% yield, orange liquid)

Benzyl isothiocyanate (836 mg, 5.60 mmol) was added to a stirred solution of sarcosine (499 mg, 5.60 mmol) in absolute ethanol (20 mL). The reaction mixture was refluxed for 3 hours and then cooled to room temperature. The mixture was extracted with ethyl acetate (10 mL) (×3). The combined organic layers were dried over anhydrous $MgSO_4$, filtered and concentrated in vacuo. The residue was purified by filtration and silica chromatography to obtain the product.

$^1$H NMR (500 MHz, DMSO-$d_6$): $\delta_H$ 7.41-7.19 (m, 5H), 4.89 (s, 2H), 4.33 (s, 2H), 3.23 (s, 3H) ppm.

(3) Synthesis of (E)-3-benzyl-5-(4-((3-hydroxypropyl)(methyl)amino)benzylidene)-1-methyl-2-thioxoimidazolidin-4-one (83 mg, 46% yield, red solid)

To a stirred solution of 3-benzyl-1-methyl-2-thioxoimidazolidin-4-one (100 mg, 0.46 mmol), 4-((3-hydroxypropyl)(methyl)amino)benzaldehyde (107 mg, 0.55 mmol) and piperidine (0.06 mL, 0.69 mmol) in 1,4-dioxane (5 mL), $AlCl_3$ (4 mg, 0.05 mmol) was added. The stirred reaction mixture was heated to 68-80° C. until the reaction was completed. The mixture was then extracted with ethyl acetate (10 mL) (×3). The combined organic layers were dried over anhydrous $MgSO_4$, filtered and concentrated in vacuo. The residue was purified by filtration and silica chromatography to obtain the product.

$^1$H NMR (500 MHz, $CDCl_3$): $\delta_H$ 8.08 (m, J=8.80 Hz, 2H), 7.53 (d, J=7.34 Hz, 2H), 7.34-7.18 (m, 3H), 6.70 (m, J=8.80 Hz, 2H), 6.44 (s, 1H), 5.28-5.06 (m, 2H), 3.71 (br. s., 2H), 3.61 (s, 3H), 3.54 (t, J=7.09 Hz, 2H), 3.10-2.98 (m, 3H), 1.85 (quin, J=6.24 Hz, 2H) ppm;

$^{13}$C NMR (125 MHz, $CDCl_3$): $\delta_C$ 174.4, 161.6, 150.7, 136.3, 133.5, 128.8, 128.4, 127.7, 125.1, 123.5, 119.9, 111.3, 60.2, 48.9, 45.1, 38.4, 30.8, 29.8 ppm; HRMS (EI) m/z $[M]^+$ calcd for $C_{22}H_{25}N_3O_2S$, 396.1, found 396.3.

Example 6. Synthesis of (E)-5-(4-((2-hydroxyethyl)(methyl)amino)benzylidene)-1-methyl-3-phenethyl-2-thioxoimidazolidin-4-one (LMT-1845)

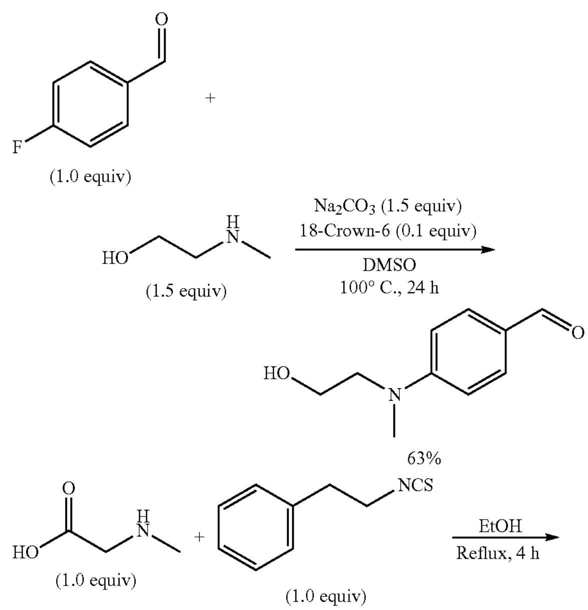

-continued

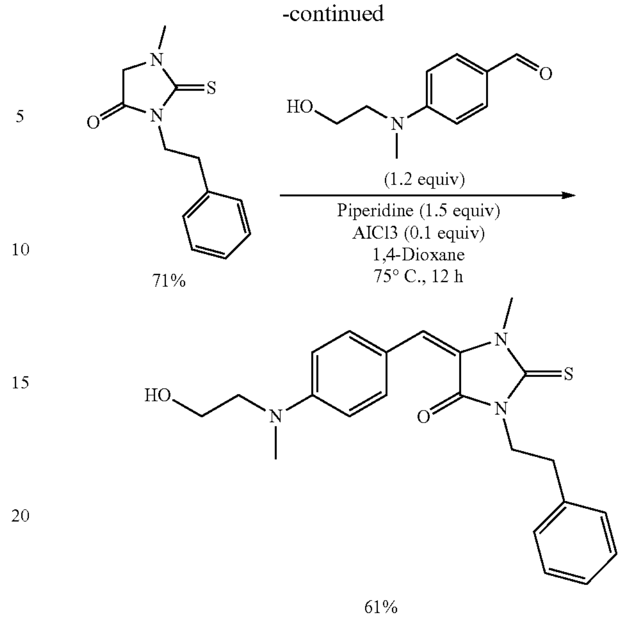

(1) Synthesis of 4-((2-hydroxyethyl)(methyl)amino)benzaldehyde (910 mg, 63% yield, yellow liquid)

To a solution of 2-(methylamino)ethanol (1.0 mL, 12.1 mmol) and $Na_2CO_3$ (1282 mg, 12.1 mmol) in DMSO (20 mL), 4-fluorobenzaldehyde (1,000 mg, 8.1 mmol) and 18-crown-6 (211 mg, 0.8 mmol) were added. The reaction mixture was stirred at 100° C. for 24 hours. The mixture was extracted with ethyl acetate (10 mL) (×3). The combined organic layers were dried over anhydrous $MgSO_4$, filtered and concentrated in vacuo. The residue was purified by filtration and silica chromatography to obtain the product.

$^1$H NMR (500 MHz, $CDCl_3$): $\delta_H$ 9.64 (d, J=1.83 Hz, 1H), 7.81-7.59 (m, 2H), 6.80-6.63 (m, 2H), 3.85 (br. s., 2H), 3.61 (t, J=5.80 Hz, 2H), 3.11 (s, 3H) ppm.

(2) Synthesis of 1-methyl-3-phenethyl-2-thioxoimidazolidin-4-one (940 mg, 71% yield, orange solid)

Phenethyl isothiocyanate (922 mg, 5.65 mmol) was added to a stirred solution of sarcosine (500 mg, 5.65 mmol) in absolute ethanol (20 mL). The reaction mixture was refluxed for 4 hours and then cooled to room temperature. The mixture was extracted with ethyl acetate (10 mL) (×3). The combined organic layers were dried over anhydrous $MgSO_4$, filtered and concentrated in vacuo. The residue was purified by filtration and silica chromatography to obtain the product.

$^1$H NMR (500 MHz, DMSO-$d_6$): $\delta_H$ 7.36-7.26 (m, 2H), 7.26-7.16 (m, 3H), 4.24 (s, 2H), 3.92-3.75 (m, 2H), 3.22 (s, 3H), 2.95-2.77 (m, 2H) ppm.

(3) Synthesis of (E)-5-(4-((2-hydroxyethyl)(methyl)amino)benzylidene)-1-methyl-3-phenethyl-2-thioxoimidazolidin-4-one (103 mg, 61% yield, orange solid)

To a stirred solution of 1-methyl-3-phenethyl-2-thioxoimidazolidin-4-one (100 mg, 0.43 mmol), 4-((2-hydroxyethyl)methyl)amino)benzaldehyde (91 mg, 0.51 mmol), and piperidine (0.06 mL, 0.65 mmol) in 1,4-dioxane (5 mL), $AlCl_3$ (4 mg, 0.04 mmol) was added. The stirred reaction mixture was heated to 68-80° C. until the reaction was completed. The mixture was then extracted with ethyl acetate (10 mL) (×3). The combined organic layers were dried over anhydrous $MgSO_4$, filtered and concentrated in vacuo. The residue was purified by filtration and silica chromatography to obtain the product.

$^1$H NMR (500 MHz, $CDCl_3$): $\delta_H$ 8.07 (d, J=9.29 Hz, 2H), 7.36-7.28 (m, 4H), 7.25-7.19 (m, 1H), 6.75 (d, J=8.80 Hz, 2H), 6.43 (s, 1H), 4.19-4.08 (m, 2H), 3.86 (d, J=4.89 Hz, 2H), 3.65-3.53 (m, 5H), 3.13-3.04 (m, 3H), 3.04-2.95 (m, 2H) ppm; $^{13}$C NMR (25 MHz, $CDCl_3$): $\delta_C$ 174.4, 161.5, 151.0, 138.3, 133.3, 129.0, 128.5, 126.5, 125.1, 123.1, 120.5, 111.6, 60.3, 54.4, 43.2, 39.0, 34.0, 30.6 ppm; HRMS (EI) m/z [M]$^+$ calcd for $C_{22}H_{25}N_3O_2S$, 364.1, found 364.3.

Example 7. Synthesis of (E)-3-benzyl-5-(2-hydroxy-4-((2-hydroxyethyl)(methyl)amino)benzylidene)-1-methyl-2-thioxoimidazolidin-4-one (LMT-2006)

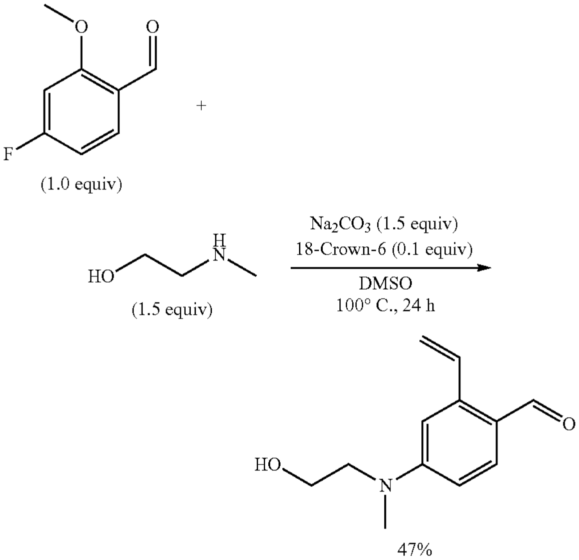

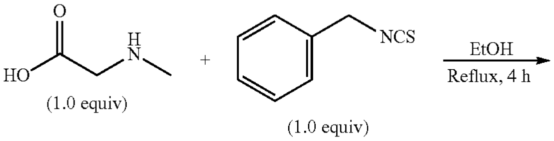

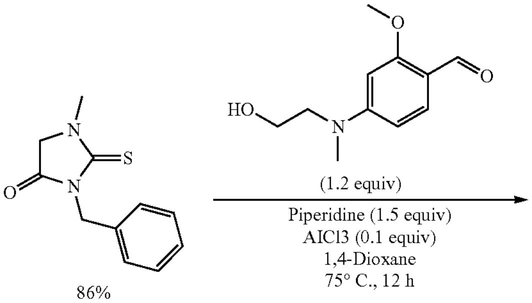

-continued

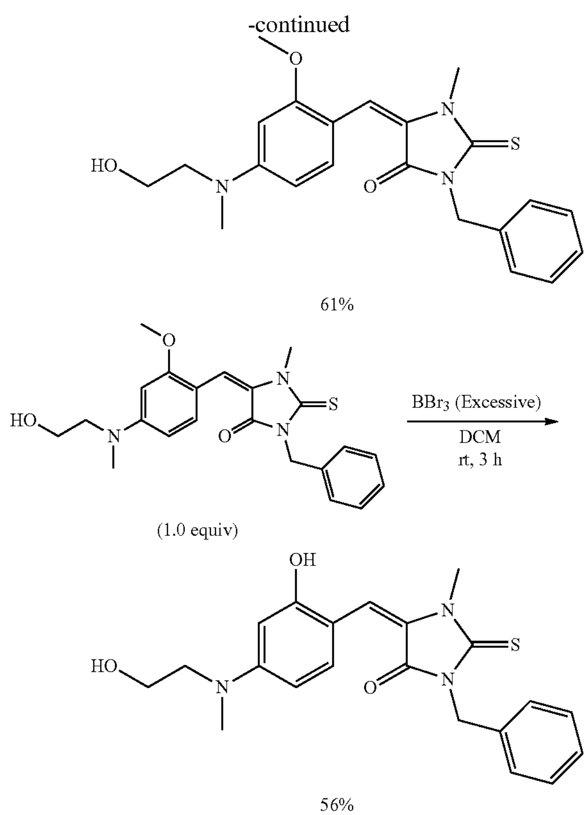

(1) Synthesis of 4-((2-hydroxyethyl)(methyl)amino)-2-methoxybenzaldehyde (318 mg, 47% yield, white solid)

To a solution of 2-(methylamino)ethanol (0.4 mL, 4.9 mmol) and $Na_2CO_3$ (515 mg, 4.9 mmol) in DMSO (20 mL), 4-fluoro-2-substituted benzaldehyde (500 mg, 3.2 mmol) and 18-crown-6 (86 mg, 0.3 mmol) were added. The reaction mixture was stirred at 100° C. for 24 hours. The mixture was extracted with ethyl acetate (10 mL) (×3). The combined organic layers were dried over anhydrous $MgSO_4$, filtered and concentrated in vacuo. The residue was purified by filtration and silica chromatography to obtain the product.

$^1$H NMR (500 MHz, DMSO-$d_6$): $\delta_H$ 10.00 (s, 1H), 7.50 (d, J=8.85 Hz, 1H), 6.39 (dd, J=9.00, 1.68 Hz, 1H), 6.21 (d, J=2.14 Hz, 1H), 4.79 (t, J=5.34 Hz, 1H), 3.87 (s, 3H), 3.58 (q, J=5.39 Hz, 2H), 3.55-3.48 (m, 2H), 3.07 (s, 3H) ppm.

(2) Synthesis of 3-benzyl-1-methyl-2-thioxoimidazolidin-4-one (1.062 g, 86% yield, orange liquid)

Benzyl isothiocyanate (836 mg, 5.60 mmol) was added to a stirred solution of sarcosine (499 mg, 5.60 mmol) in absolute ethanol (20 mL). The reaction mixture was refluxed for 3 hours and then cooled to room temperature. The mixture was extracted with ethyl acetate (10 mL) (×3). The combined organic layers were dried over anhydrous $MgSO_4$, filtered and concentrated in vacuo. The residue was purified by filtration and silica chromatography to obtain the product. $^1$H NMR (500 MHz, DMSO-$d_6$): $\delta_H$ 7.41-7.19 (m, 5H), 4.89 (s, 2H), 4.33 (s, 2H), 3.23 (s, 3H) ppm.

(3) Synthesis of (E)-3-benzyl-5-(4-((2-hydroxyethyl)(methyl)amino)-2-methoxybenzylidene)-1-methyl-2-thioxoimidazolidin-4-one (114 mg, 61% yield, orange solid)

To a stirred solution of 3-benzyl-1-methyl-2-thioxoimidazolidin-4-one (100 mg, 0.45 mmol), 4-((2-hydroxyethyl)(methyl)amino)-2-methoxybenzaldehyde (113 mg, 0.54 mmol), and piperidine (0.07 mL, 0.68 mmol) in 1,4-dioxane (5 mL), $AlCl_3$ (5 mg, 0.05 mmol) was added. The stirred reaction mixture was heated to 68-80° C. until the reaction was completed. The mixture was then extracted with ethyl acetate (10 mL) (×3). The combined organic layers were dried over anhydrous $MgSO_4$, filtered and concentrated in vacuo. The residue was purified by filtration and silica chromatography to obtain the product.

$^1H$ NMR; $\delta_H$ 8.64 (d, J=9.0 Hz, 1H), 7.52 (d, J=7.1 Hz, 2H), 7.30-7.22 (m, J=14.6, 7.2 Hz, 4H), 7.00 (s, 1H), 6.39 (dd, J=9.0, 2.3 Hz, 1H), 6.19 (d, J=2.2 Hz, 1H), 5.15 (s, 2H), 3.91-3.82 (m, 5H), 3.62 (s, 3H), 3.58 (t, J=5.6 Hz, 2H), 3.08 (d, J=11.1 Hz, 3H) ppm.

(4) Synthesis of (E)-3-benzyl-5-(2-hydroxy-4-((2-hydroxyethyl)(methyl)amino)benzylidene)-1-methyl-2-thioxoimidazolidin-4-one (17 mg, 56% yield, orange solid)

A solution of (E)-3-benzyl-5-(4-((2-hydroxyethyl)(methyl)amino)-2-methoxybenzylidene)-1-methyl-2-thioxoimidazolidin-4-one in anhydrous dichloromethane was cooled in a dry ice/acetone bath under a nitrogen atmosphere. $BBr_3$ (0.05 mL, 0.6 mmol) was added dropwise. The cooling bath was removed and the reaction mixture was stirred at room temperature for 3 hours. The mixture was cooled on an ice bath and excess $BBr_3$ was quenched by dropwise addition of methanol. The resulting solution was stirred at room temperature for 2 hours. After removing the solvent, the residue was treated with $H_2O$ (10 mL) and ethyl acetate (10 mL). The combined organic layers were washed with $H_2O$, dried over $Na_2SO_4$ and concentrated. The residue was purified by silica chromatography to obtain the product.

$^1H$ NMR (500 MHz, DMSO-$d_6$): $\delta_H$, 8.69 (d, J=9.1 Hz, 1H), 7.35-7.30 (m, 4H), 7.26 (t, J=6.6 Hz, 1H), 7.11 (s, 1H), 6.28 (d, J=9.1 Hz, 1H), 6.19 (s, 1H), 5.05 (s, 2H), 4.78 (s, 1H), 3.61-3.51 (m, 5H), 3.43 (t, J=5.8 Hz, 2H), 2.97 (d, J=13.1 Hz, 3H) ppm; $^{13}C$ NMR (125 MHz, DMSO-$d_6$): $\delta_C$ 172.7, 161.4, 153.4, 137.1, 132.3, 128.8, 128.0, 127.7, 123.0, 119.1, 108.3, 104.2, 97.3, 58.6, 54.3, 44.8, 31.1 ppm; HRMS (EI) m/z $[M]^+$ calcd for $C_{21}H_{23}N_3O_3S$, 398.2, found 398.2.

Example 8. Synthesis of (E)-3-benzyl-5-(4-((3-hydroxypropyl)(methyl)amino)-2-methoxybenzylidene)-1-methyl-2-thioxoimidazolidin-4-one (LMT-2007)

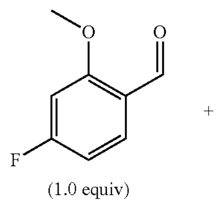

+

-continued

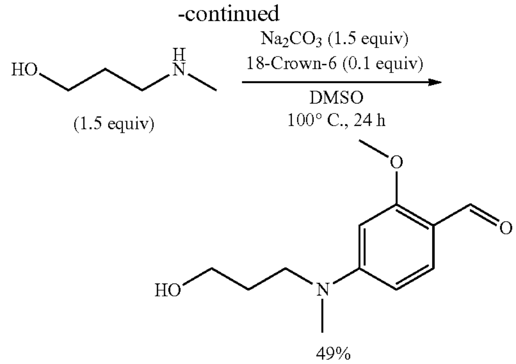

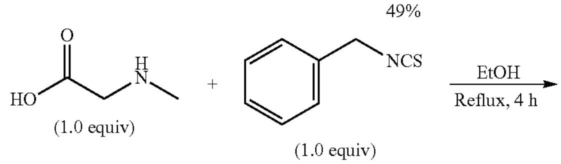

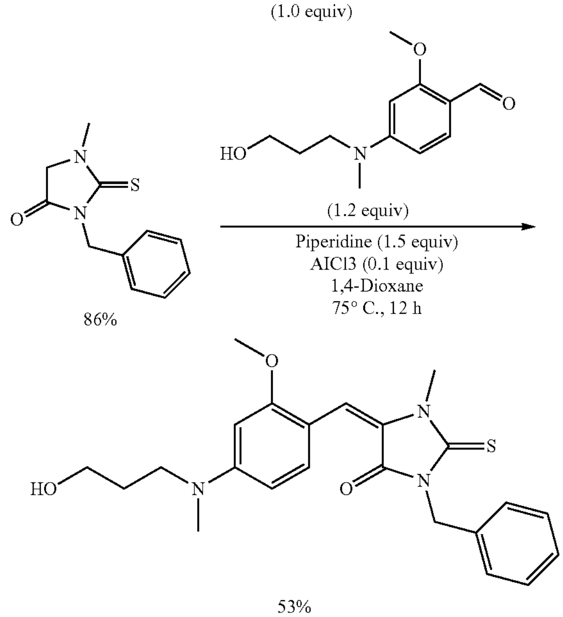

(1) Synthesis of 4-((3-hydroxypropyl)(methyl)amino)-2-methoxybenzaldehyde (177 mg, 49% yield, white solid)

To a solution of 3-(methylamino)propanol (0.4 mL, 2.4 mmol) and $Na_2CO_3$ (256 mg, 2.4 mmol) in DMSO (10 mL), 4-fluoro-2-substituted benzaldehyde (250 mg, 1.6 mmol) and 18-crown-6 (45 mg, 0.2 mmol) were added. The reaction mixture was stirred at 100° C. for 24 hours. The mixture was extracted with ethyl acetate (10 mL) (×3). The combined organic layers were dried over anhydrous $MgSO_4$, filtered and concentrated in vacuo before use in the next reaction.

(2) Synthesis of 3-benzyl-1-methyl-2-thioxoimidazolidin-4-one (1.062 g, 86% yield, orange liquid)

Benzyl isothiocyanate (836 mg, 5.60 mmol) was added to a stirred solution of sarcosine (499 mg, 5.60 mmol) in absolute ethanol (20 mL). The reaction mixture was refluxed for 3 hours and then cooled to room temperature. The mixture was extracted with ethyl acetate (10 mL) (×3). The combined organic layers were dried over anhydrous $MgSO_4$, filtered and concentrated in vacuo. The residue was purified by filtration and silica chromatography to obtain the product.

$^1H$ NMR (500 MHz, DMSO-$d_6$): $\delta_H$ 7.41-7.19 (m, 5H), 4.89 (s, 2H), 4.33 (s, 2H), 3.23 (s, 3H) ppm.

(3) Synthesis of (E)-3-benzyl-5-(4-((3-hydroxypropyl)(methyl)amino)-2-methoxybenzylidene)-1-methyl-2-thioxoimidazolidin-4-one (99 mg, 53% yield, orange solid)

To a stirred solution of 3-benzyl-1-methyl-2-thioxoimidazolidin-4-one (100 mg, 0.45 mmol), 4-((3-hydroxypropyl)(methyl)amino)-2-methoxybenzaldehyde (121 mg, 0.54 mmol), and piperidine (0.07 mL, 0.68 mmol) in 1,4-dioxane (5 mL), $AlCl_3$ (5 mg, 0.05 mmol) was added. The stirred reaction mixture was heated to 68-80° C. until the reaction was completed. The mixture was then extracted with ethyl acetate (10 mL) (×3). The combined organic layers were dried over anhydrous $MgSO_4$, filtered and concentrated in vacuo. The residue was purified by filtration and silica chromatography to obtain the product.

$^1H$ NMR (500 MHz, $CDCl_3$): $\delta_H$ 8.67 (d, J=9.0 Hz, 1H), 7.51 (d, J=7.2 Hz, 2H), 7.28 (t, J=7.1 Hz, 2H), 7.23 (d, J=7.0 Hz, 1H), 7.02 (s, 1H), 6.36 (d, J=8.8 Hz, 1H), 6.15 (s, 1H), 5.14 (s, 2H), 3.85 (s, 3H), 3.68 (t, J=5.4 Hz, 2H), 3.61 (s, 3H), 3.53 (t, J=6.6 Hz, 2H), 3.02 (s, 3H) ppm; $^{13}C$ NMR (125 MHz, $CDCl_3$): $\delta_C$ 173.9, 161.6, 160.2, 152.9, 136.4, 132.5, 128.7, 128.4, 127.6, 124.5, 117.9, 109.3, 104.2, 93.5, 77.3, 77.1, 76.8, 59.9, 55.5, 49.0, 45.1, 38.4, 30.9, 30.0 ppm; HRMS (EI) m/z $[M]^+$ calcd for $C_{22}H_{25}N_3O_3S$, 426.2, found 426.2.

Experimental Example 1. Lucigenin Chemiluminescence Assay

Experiment Method

Human Nox isozymes were provided from transgenic flies expressing human Nox isozymes under the daughterless (Da)-GAL4 promoter. The genotype of each fly line is shown below.

1) Human Nox1: UAS-hNox1/UAS-dDuox-RNAi; Da-GAL4/+
2) Human Nox2: UAS-hNox2/UAS-dDuox-RNAi; Da-GAL4/+
3) Human Nox4: UAS-hNox4/UAS-dDuox-RNAi; Da-GAL4/+

Transgenic flies were homogenized with PBS containing protease inhibitors (Aprotinin and Leupeptin) to obtain Drosophila membranes of each Nox isozyme. The membranes were incubated with compounds (100 μM, 10 μM, 1 μM, 0.1 μM, 0.01 μM, 0.001 μM, and 0 μM) for 10 min on a shaker. After that, a mixture of 500 μM NADPH (beta-nicotinamide adenine dinucleotide 2'-phosphate reduced tetrasodium salt hydrate; Sigma-Aldrich) and 400 μM lucigenin (N,N'-dimethyl-9,9'-biacridinium dinitrate; Sigma-Aldrich) in 1× HEPES (4-(2-hydroxyethyl)-1-piperazineethanesulfonic acid) buffer was added to the membrane. Lucigenin chemiluminescence was detected at 1 minute intervals for 10 min using a multimode microplate reader (SpectraMax iD3, Molecular Devices). $IC_{50}$ values were calculated with Graph-Pad Prism 5 (GraphPad Software).

(1) Results of Measuring $IC_{50}$ Values of Nox Inhibitory Compounds

Lucigenin chemiluminescence assays were performed with Drosophila membranes expressing hNox1, hNox2 and hNox4. The assay was repeated three times and the average of the $IC_{50}$ values was determined.

Table 1 and FIG. 1 below show results of the compounds of Examples 1, 2 and 4 according to the present invention.

TABLE 1

| | $IC_{50}$ (μM) | | |
|---|---|---|---|
| | Nox1 | Nox2 | Nox4 |
| Example 1 | 1.45 | 1.89 | 2.46 |
| Example 2 | 1.49 | 1.84 | 1.72 |
| Example 4 | — | 0.52 | 1.4 |

Figure 2:
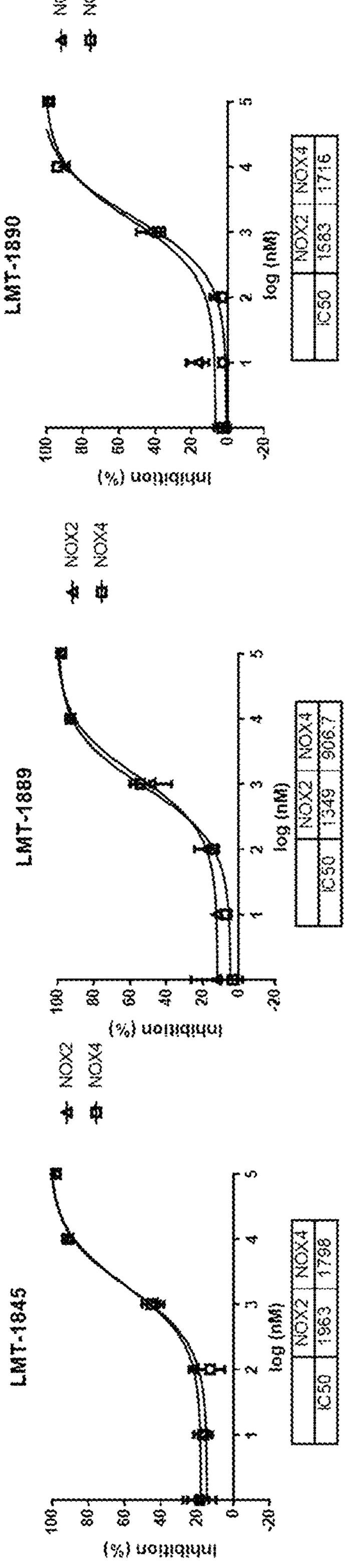
FIG. 2 shows $IC_{50}$ value measurement results of the compounds according to the present invention for confirming the Nox inhibitory effect.
Figure 2:
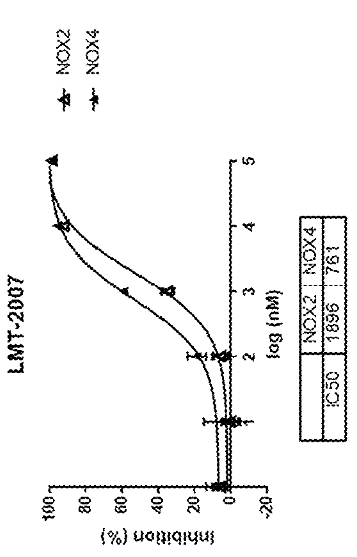
Figure 2:
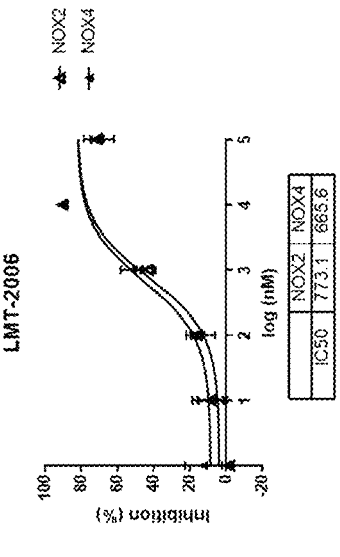

In addition, Table 2 and FIG. 2 below show results of the compounds of Examples 3, 5, 6, 7 and 8 according to the present invention. With respect to Examples 3, 5, 6, 7, and 8 above, the actions on Nox2 and Nox4 were confirmed.

TABLE 2

| | $IC_{50}$ (μM) | |
|---|---|---|
| | Nox2 | Nox4 |
| Example 3 | 1.583 | 1.716 |
| Example 5 | 1.349 | 0.9067 |
| Example 6 | 1.963 | 1.798 |
| Example 7 | 0.773 | 0.665 |
| Example 8 | 1.896 | 0.761 |

(2) Analysis Result of Nox Inhibitory Effect on Compounds of Example 1 and Example 2 in BV2 Cells BV2 cells were washed with Hank's balanced salt solution (HBSS) and incubated in HBSS at 37° C. for 30 minutes. Then, the cells were treated with the compound (compound of Example 1 or compound of Example 2) at various concentrations (0 nM, 1 nM, 10 nM, 100 nM, 1000 nM, and 10000 nM). After 30 minutes, 200 ng/ml of lipopolysaccharide (LPS) and 200 μM of lucigenin were added to the cells. Lucigenin chemiluminescence was detected at 10 second intervals for 15 minutes using a luminometer (GLOMA, Promega).

Specifically, BV2 cells were pre-treated with Compound (A) of Example 1 or Compound (B) of Example 2 for 30 minutes and generation of reactive oxygen species (ROS) was detected after treatment with LPS (200 ng/ml). Data are expressed as mean±SD (N=3). Experimental results thereof are shown in FIG. 3.

Figure 3:
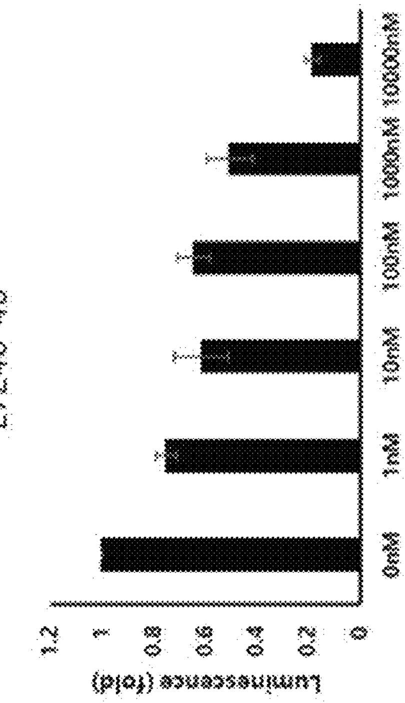
FIG. 3 shows the Nox inhibitory effect analysis results of the compound of Example 1 (E7240-17) and the compound of Example 2 (E7240-40) in BV2 cells.
Figure 3:
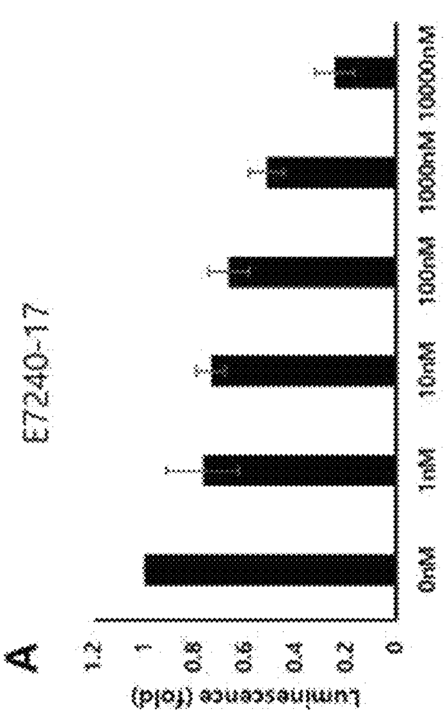

As could be confirmed in FIG. 3, treatment with the compound (E7240-17) of Example 1 and the compound (E7240-40) of Example 2 according to the present invention exhibited an excellent Nox inhibitory effect, resulting in a significant inhibition of ROS generation.

Experimental Example 2. Experiments as to Compound Treatment Against MPTP-Induced Parkinson's Disease

(1) Experiment Method

1) Efficacy Analysis Experiment of Compound Against MPTP-induced Parkinson's Disease In order to evaluate the effect of the compound of Example 1 against MPTP (1-methyl-4-phenyl-1,2,3,6-tetrahydropyridine hydrochloride; Sigma-Aldrich) induced Parkinson's disease, twenty-six C57BL/6 male mice (9 weeks old) were randomly divided into three groups.

(1) saline+vehicle (2) MPTP+vehicle (3) MPTP+compound of Example 1 (10 mg/kg)

Mice were injected intraperitoneally with MPTP (15 mg/kg) 4 times at 2 hour intervals, whereas control mice were treated with the same volume of saline. The compound of Example 1 was dissolved in a vehicle containing 4% DMSO (dimethyl sulfoxide, Sigma-Aldrich) and 96% corn oil (Sigma-Aldrich). Mice received daily intraperitoneal injections of the compound of Example 1 at 10 mg/kg for 8 days from 1 day prior to MPTP injection.

2) Immunohistochemical Staining Test

Dopaminergic neurons were detected using an anti-tyrosine hydroxylase antibody (1:2000-4000, abcaom) and microglia were measured using an anti-Iba1 antibody (1:1000, Wako). Biotinylated goat anti-rabbit antibody (VECTOR, BA-1000) was used as secondary antibody, and ABC solution (VECTOR, BA-1000) was employed. The immunoreactive regions were then incubated with 3-3' diaminobenzidine (DAB, Dako) to change the color to brown.

Seven days post MPTP injection (one day post the final injection of the compound of Example 1), mice were sacrificed and brains thereof were recovered. The brain was sectioned coronally (thickness of 30 μm) using a cryostat (CM1850, Leica), and stored in anti-freeze solution (30% sucrose, 1% polyvinylpyrrolidone and 30% ethylene glycol in 1×PBS) at −20° C.

Six coronal sections from substantia nigra (bregma −2.80 mm to −3.80 mm) and three coronal sections (bregma +0.98 mm to +0.50 mm) were collected every 150 μm, stained, and analyzed using ImagePro plus 7.0 software.

3) Behavioral Test (Rotarod Test)

Mice were subjected to the rotarod test 3 times (1 day before MPTP injection, Day 3 and Day 6 post MPTP injection) based on 3 trials/day. The rotarod speed was gradually increased from 4 RPM to 40 RPM and the retention time on the rod was analyzed.

(2) Experimental Results on Compound of Example 1

Figure 4:
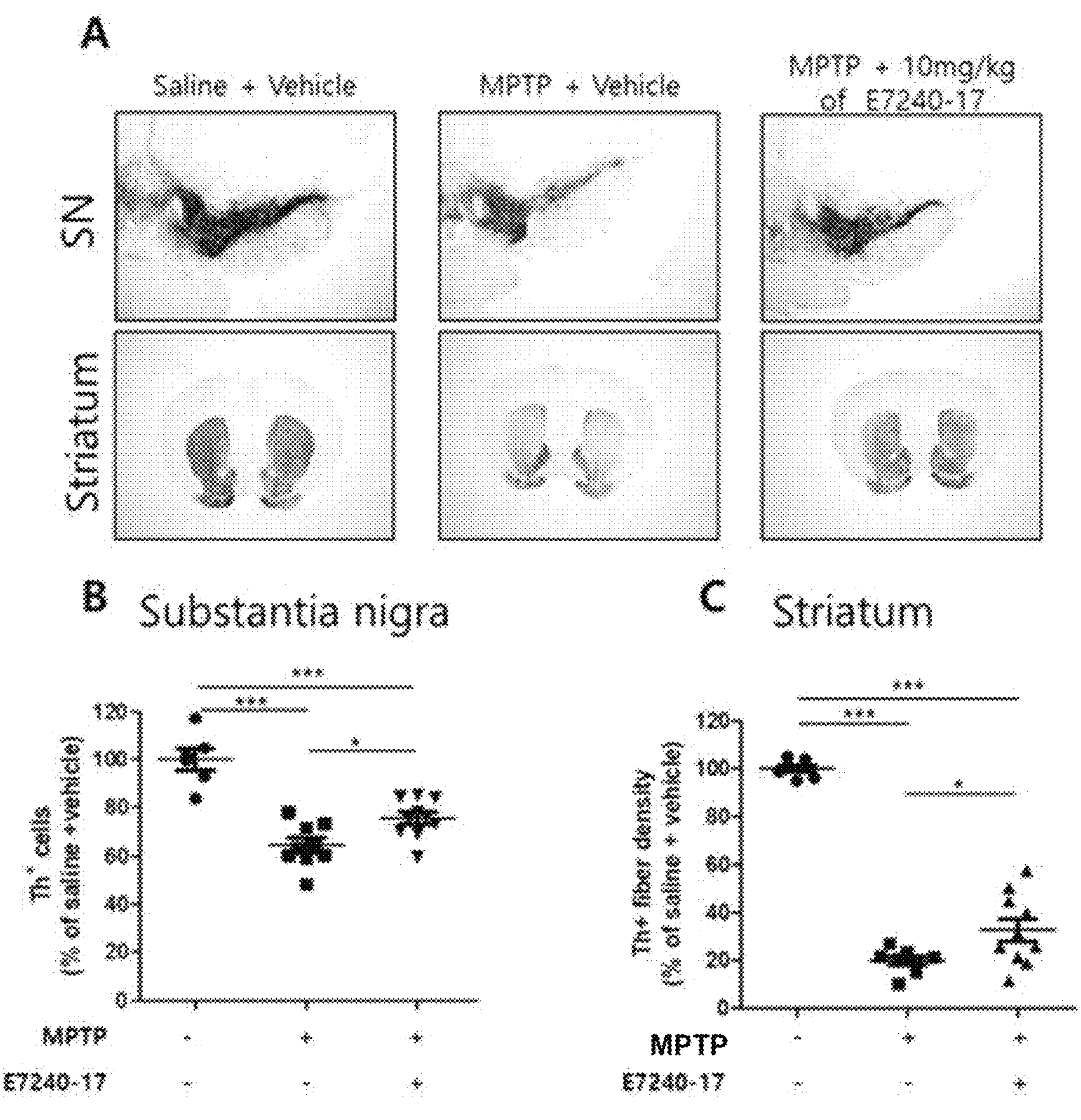
FIG. 4 shows results of the treatment effect confirmed by treatment with the compound of Example 1 in the MPTP-induced Parkinson's disease model mice.

1) Experimental Results of Treatment with Compound of Example 1 Against MPTP-induced Parkinson's Disease The compound of Example 1 protected dopaminergic neurons in MPTP-induced Parkinson's disease. FIG. 4 shows (A) representative tyrosine hydroxylase (Th) immunostaining images of the substantia nigra and striatum, (B) the counts of 6 sections of $Th^+$ cells in the substantia nigra, and (C) $Th^+$ fiber density of 3 sections in the striatum. Asterisks indicate significant differences. (Determined by Student's t-test *p<0.05, ***p<0.0005)

Treatment with the compound according to the present invention showed an excellent effect on dopaminergic neuron protection, as could be confirmed through each of the above experimental results.

2) Immunohistochemical Staining Result

Figure 5:
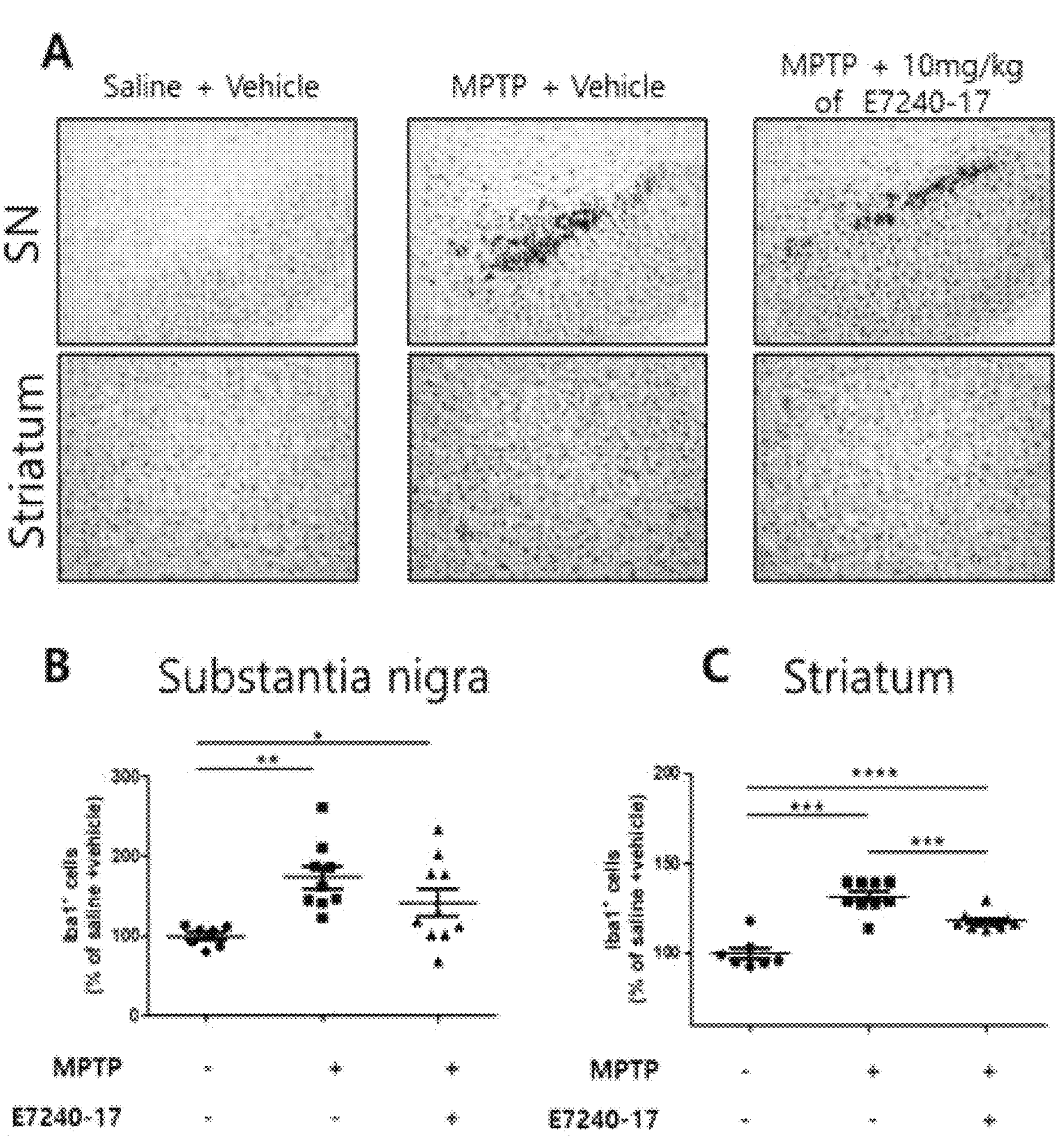
FIG. 5 shows immunohistochemical staining results according to the treatment with the compound of Example 1 in the MPTP-induced Parkinson's disease model mice.

The compound of Example 1 improved the pathology of microglia in MPTP-induced Parkinson's disease. FIG. 5 shows (A) representative Iba1 immunostained images of the substantia nigra and striatum, and the counts of $Iba1^+$ in substantia nigra (B) and striatum (C). Asterisks indicate significant differences. (Determined by Student's t-test *p<0.05, p<0.005, *p<0.0005)

Treatment with the compound according to the present invention showed an excellent effect on improving the pathology of microglia.

3) Behavioral Test Result

Figure 6:
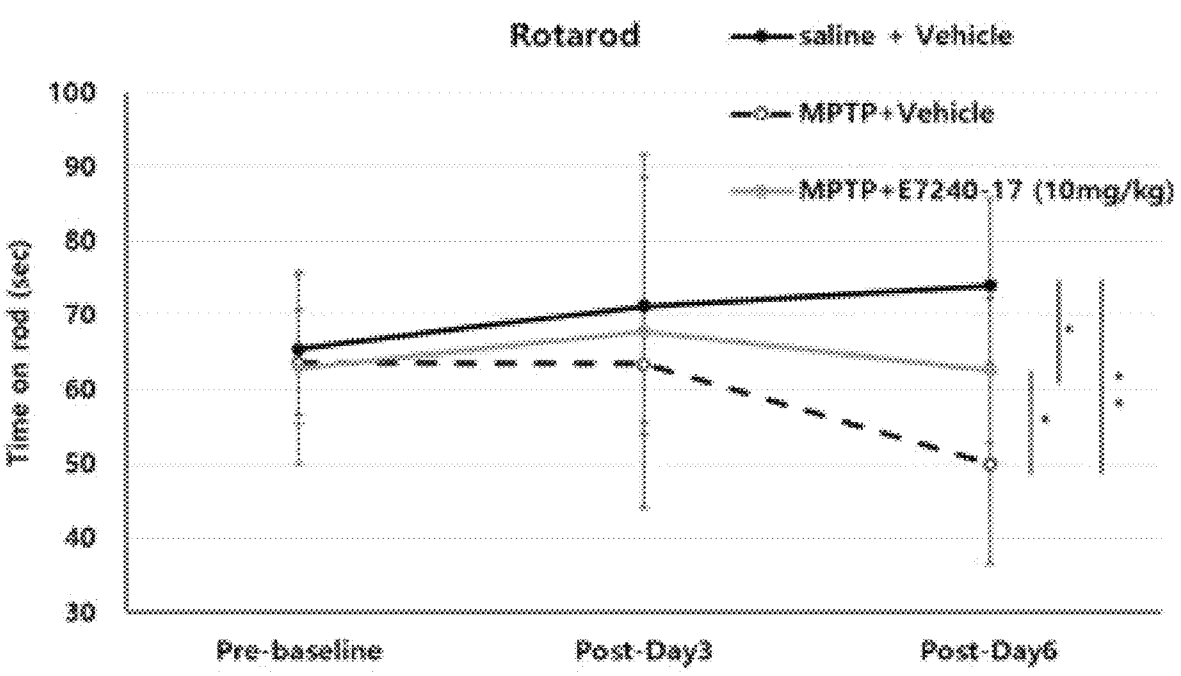
FIG. 6 shows the behavioral test results according to the treatment with the compound of Example 1 in the MPTP-induced Parkinson's disease model mice.

The compound of Example 1 improved motor function in MPTP-induced Parkinson's disease. The retention time on the rod was evaluated by the rotarod test 1 day before MPTP injection, Day 3 and Day 6 post MPTP injection and shown in FIG. 6. Data were expressed as mean±SD. Asterisks indicated significant differences. (Determined by Student's t-test *p<0.05, ***p<0.005)

The treatment with the compound according to the present invention showed an excellent improvement effect by significantly increasing the staying time on the rod even in the rotarod test.

Experimental Example 3. Experiments as to Compound Treatment on Huα-Syn Transgenic Mice (1) Experiment Method In order to evaluate the effect of the compound of Example 1 on Huα-Syn transgenic mice, 6-month-old transgenic mice or wild-type mice were divided into 4 groups.

(1) wild type (WT)+vehicle (2) transgenic (TG)+vehicle (3) wild type+compound of Example 1 (10 mg/kg)

(4) transgenic+compound of Example 1 (10 mg/kg)

The compound of Example 1 was dissolved in a vehicle containing 4% DMSO (dimethyl sulfoxide, Sigma-Aldrich) and 96% corn oil (Sigma-Aldrich). Mice were intraperitoneally injected with the compound of Example 1 daily at 10 mg/kg daily for 3 months.

(2) Experimental Results on Huα-Syn Transgenic Mice According to Administration of Compound of Example 1

Figure 7:
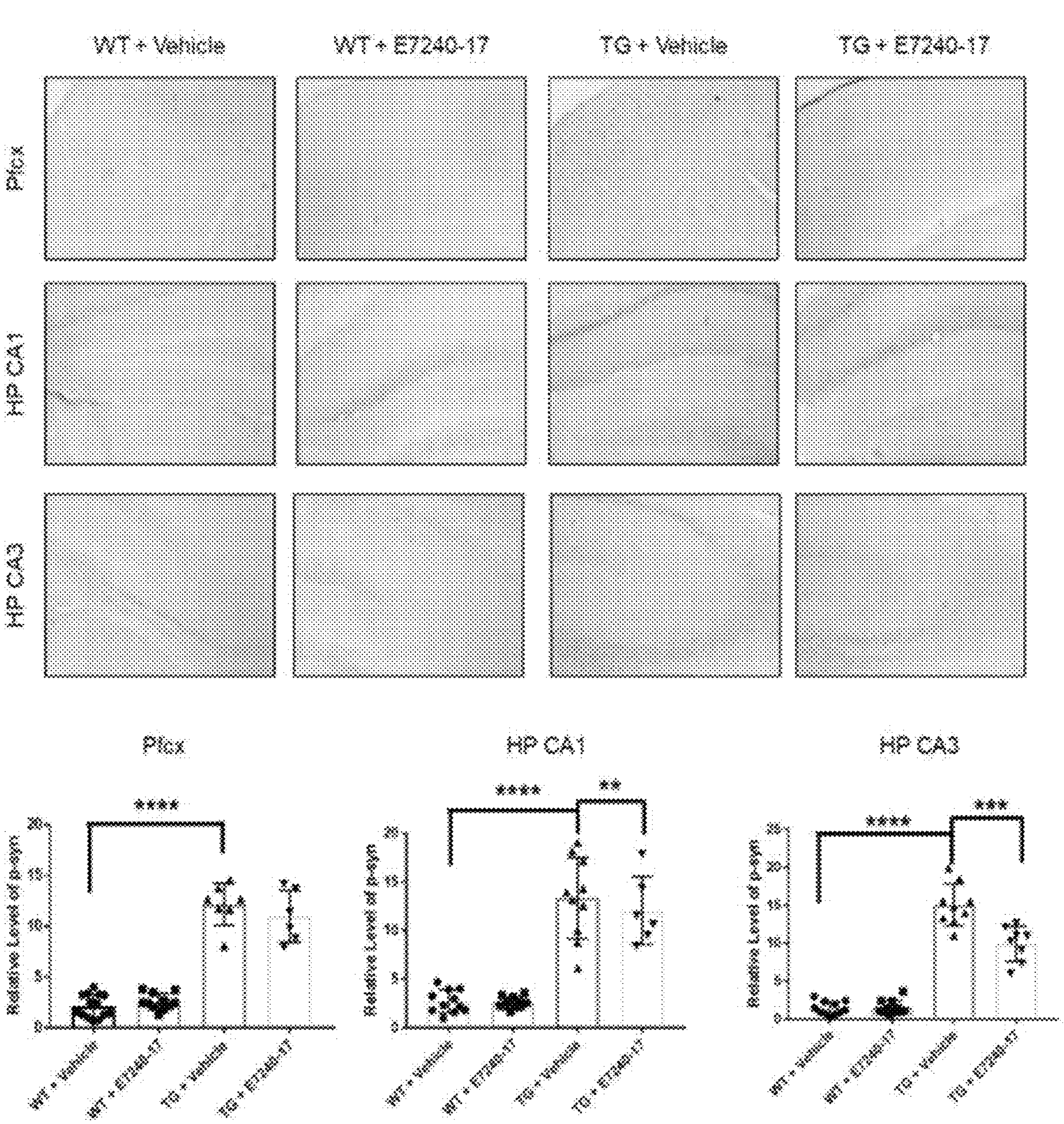
FIG. 7 shows a comparison of the amount of the phosphor α-synuclein in the hippocampus (HP CA1, HP CA2) of Huα-Syn transgenic mice according to administration of the compound of Example 1.

Experimental results thereof are shown in FIG. 7. The compound of Example 1 reduced the amount of the phosphor α-synuclein (syn) in Huα-Syn transgenic mice. Specifically, the phosphor α-synuclein immunoreactivity was significantly increased in both the prefrontal cortex (Pfcx) and hippocampi (HP) of transgenic mice. However, a 3-month treatment with the compound of Example 1 reduced the amount of the phosphor α-synuclein in the hippocampus (HP CA1, HP CA2) compared to vehicle-treated Huα-Syn transgenic mice.

Figure 8:
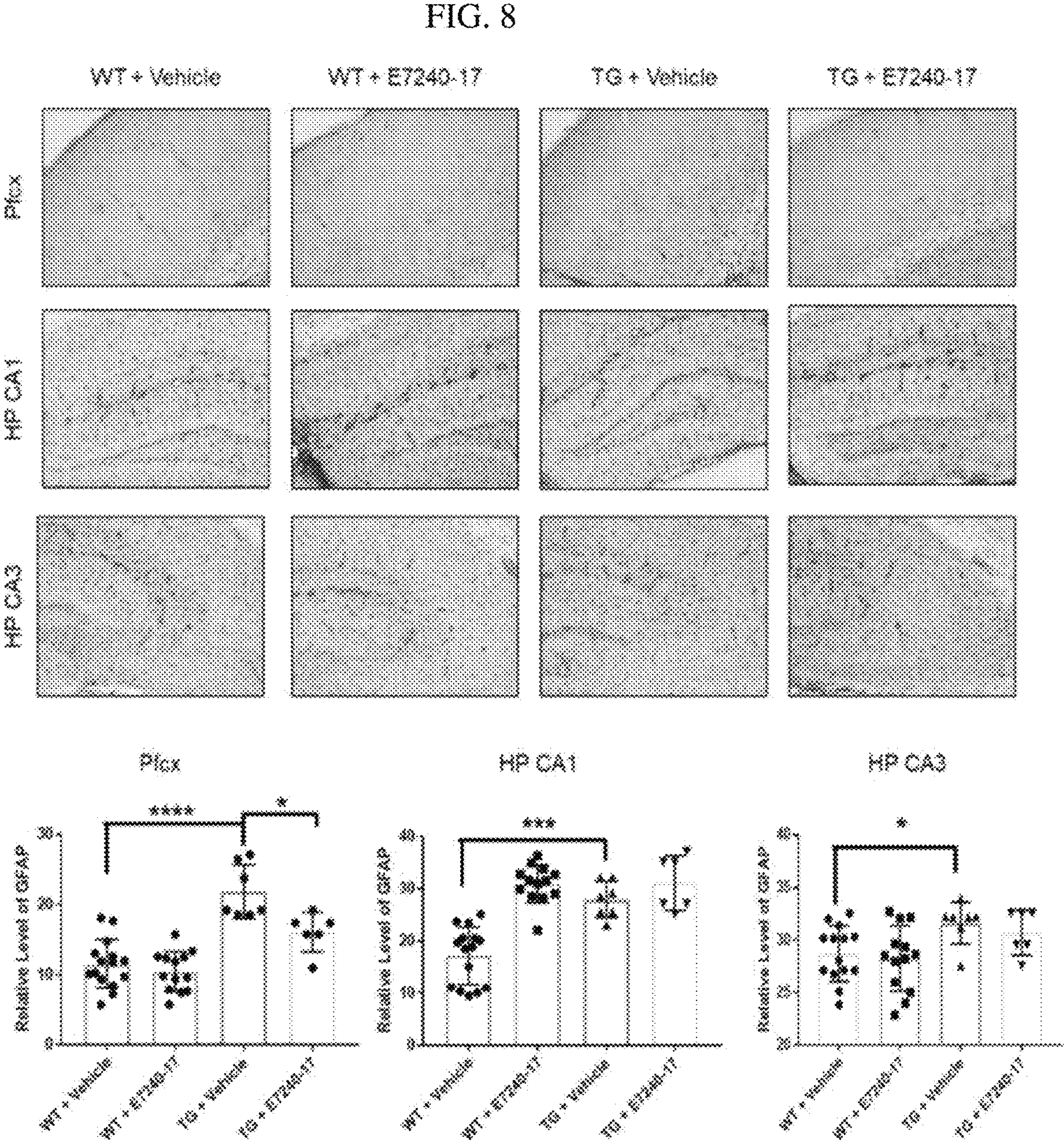
FIG. 8 shows results of astrocyte pathology in the prefrontal cortex (Pfcx) of Huα-Syn transgenic mice according to the administration of the compound of Example 1.

In addition, as shown in FIG. 8, the compound of Example 1 improved astrocyte pathology in the prefrontal cortex (Pfcx) of Huα-Syn transgenic mice. Huα-Syn transgenic mice expressed a significantly increased amount of GFAP immunopositive astrocytes. Transgenic mice treated with the compound of Example 1 exhibited reduced astrocytes in Pfcx compared to the vehicle-treated Huα-Syn transgenic mice.

Figure 9:
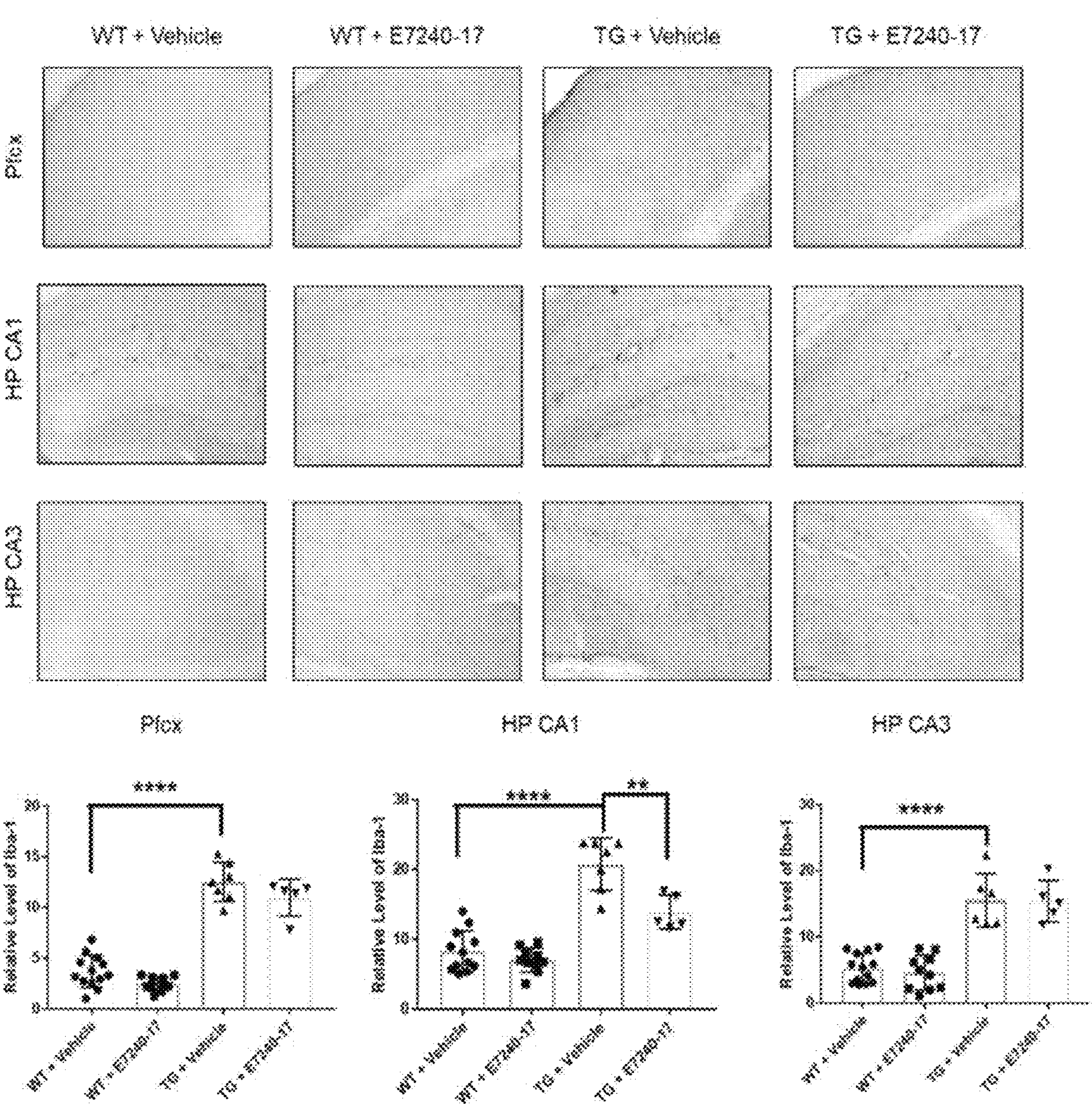
FIG. 9 shows results of microglia pathology of hippocampus (HP CA1) of Huα-Syn transgenic mice according to the administration of the compound of Example 1.

Further, as shown in FIG. 9, the compound of Example 1 improved microglia pathology in the hippocampus (HP CA1) of Huα-Syn transgenic mice. In transgenic mice in which Iba1 immuno-positive microglia increased in Pfcx and hippocampus, treatment with the compound of Example 1 showed a decrease in the number of microglial cells in HP CA1 compared to the vehicle-treated Huα-Syn transgenic mice.

Figure 10:
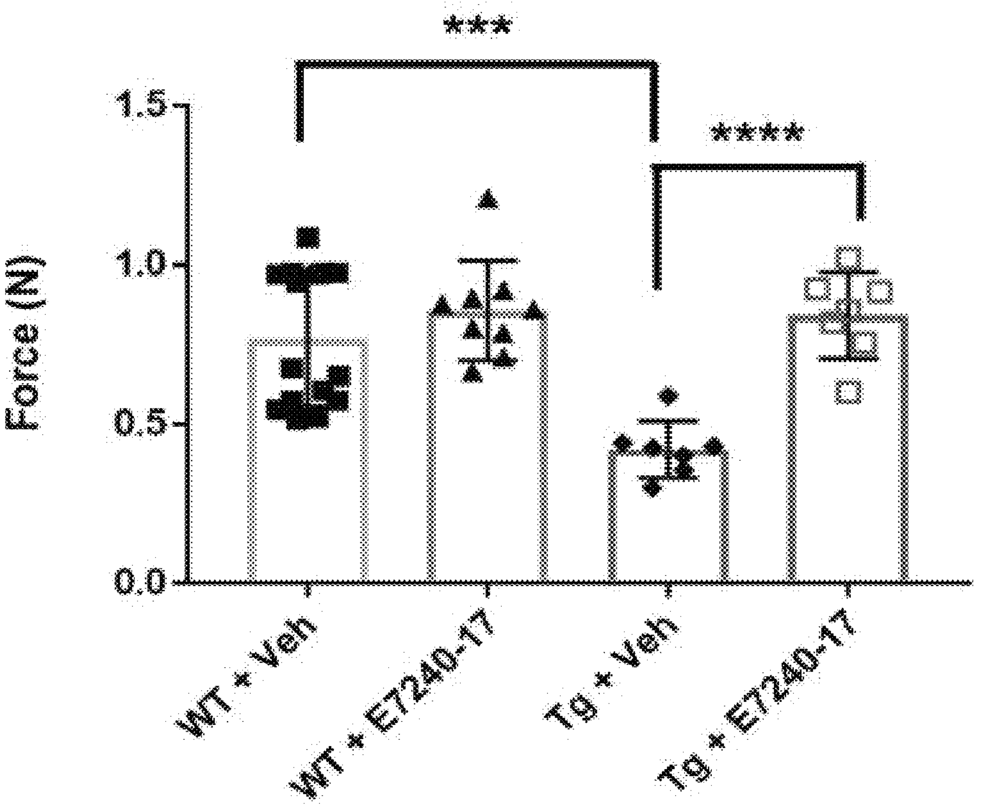
FIG. 10 shows the degree of improvement in neuromuscular function of Huα-Syn transgenic mice according to the administration of the compound of Example 1.

In addition, as shown in FIG. 10, the compound of Example 1 improved neuromuscular function of Huα-Syn transgenic mice. The maximum force of the mouse forelimb was recorded with a grip strength meter. The grip strength of vehicle-treated transgenic mice was reduced compared to wild-type mice of the same age. The 3-month treatment with the compound of Example 1 improved the grip strength of Huα-Syn transgenic mice.

Experimental Example 4. Treatment of Compound of Example 2 Against PFF-Induced Parkinson's Disease In order to develop preformed fibrils (PFF)-induced Parkinson's disease, 8-12 week old C57BL/6 mice were stereotaxically inoculated with 5 μg of PFF into the right dorsal striatum (AP+0.2 mm, ML+0.2 mm, DV 2.6 mm). Five months post single inoculation of PFF, animals were intraperitoneally injected with the compound of Example 2 at 10 mg/kg daily for 3 months.

Figure 11:
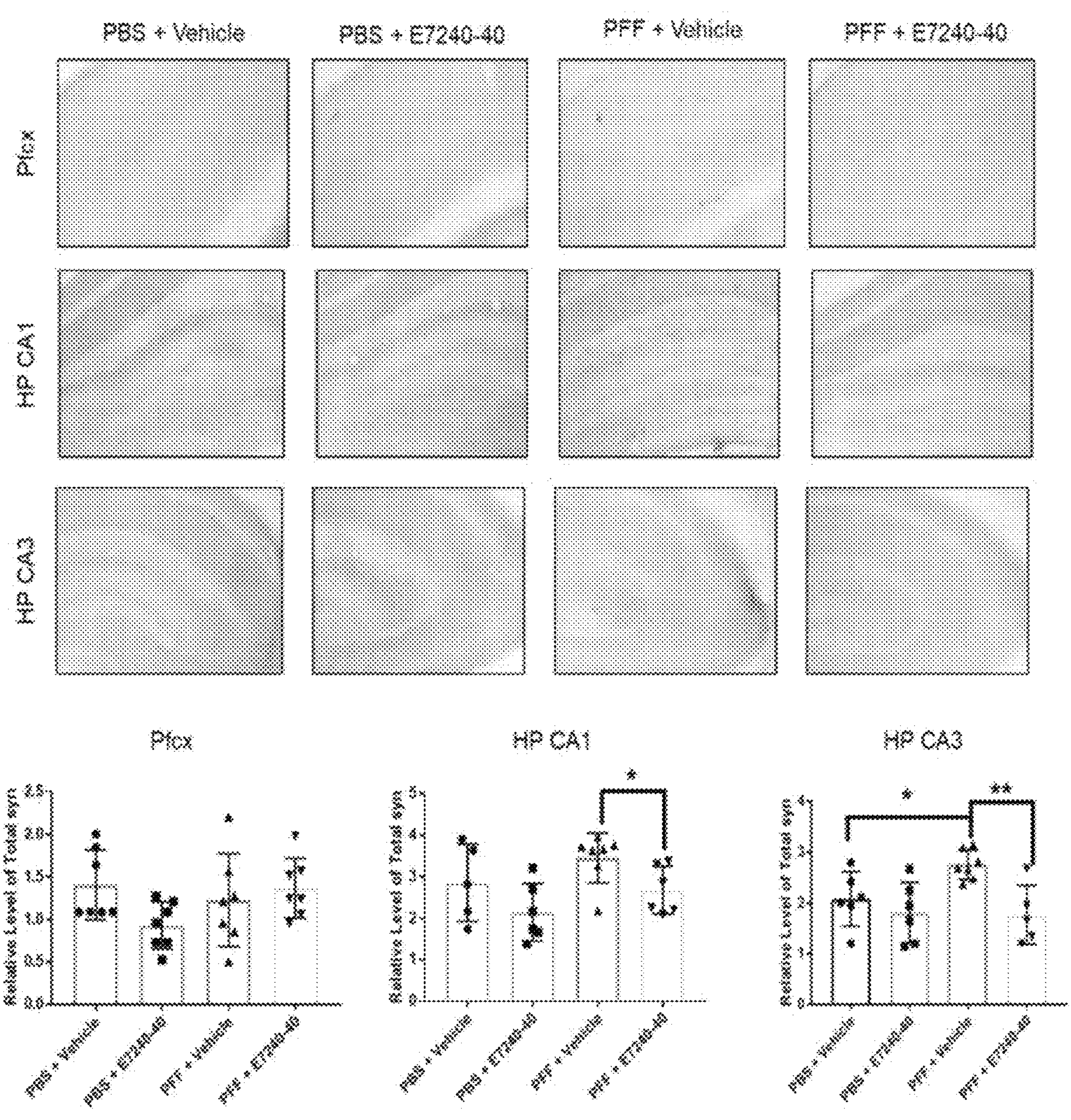
FIG. 11 shows a comparison of the amount of α-synuclein in PFF-injected mice according to administration of the compound of Example 2.

Specifically, as shown in FIG. 11, the compound of Example 2 decreased the amount of α-synuclein in the hippocampus (HP CA1, HP CA3) of PFF-injected mice. Accumulation of α-synuclein in the hippocampus was increased in the vehicle-treated PFF-injected mice. On the other hand, the amount of α-synuclein was significantly decreased in the hippocampus (HP CA1, HP CA3) by the administration of the compound of Example 2 for 3 months.

Figure 12:
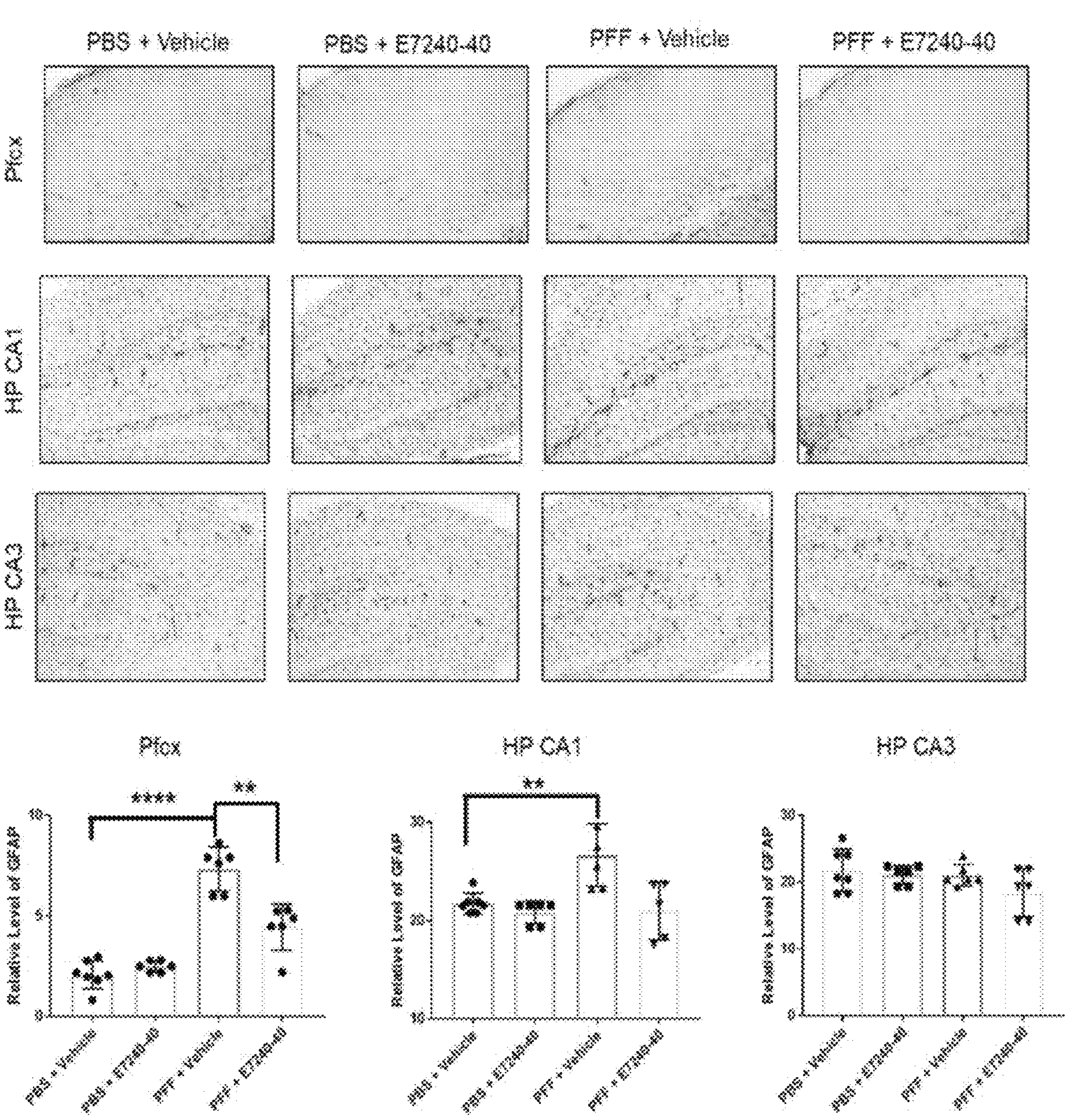
FIG. 12 shows results of astrocyte pathology in the prefrontal cortex (Pfcx) of PFF-injected mice according to the administration of the compound of Example 2.

In addition, as shown in FIG. 12, the compound of Example 2 improved astrocyte pathology in the prefrontal cortex (Pfcx) of PFF-injected mice. A single injection of PFF (5 μg) increased GFAP immuno-positive astrocytes in both the Pfcx and hippocampus (HP CA1). The 3-month treatment with the compound of Example 2 reduced GFAP immuno-positive astrocytes in the Pfcx of PFF-injected mice.

Figure 13:
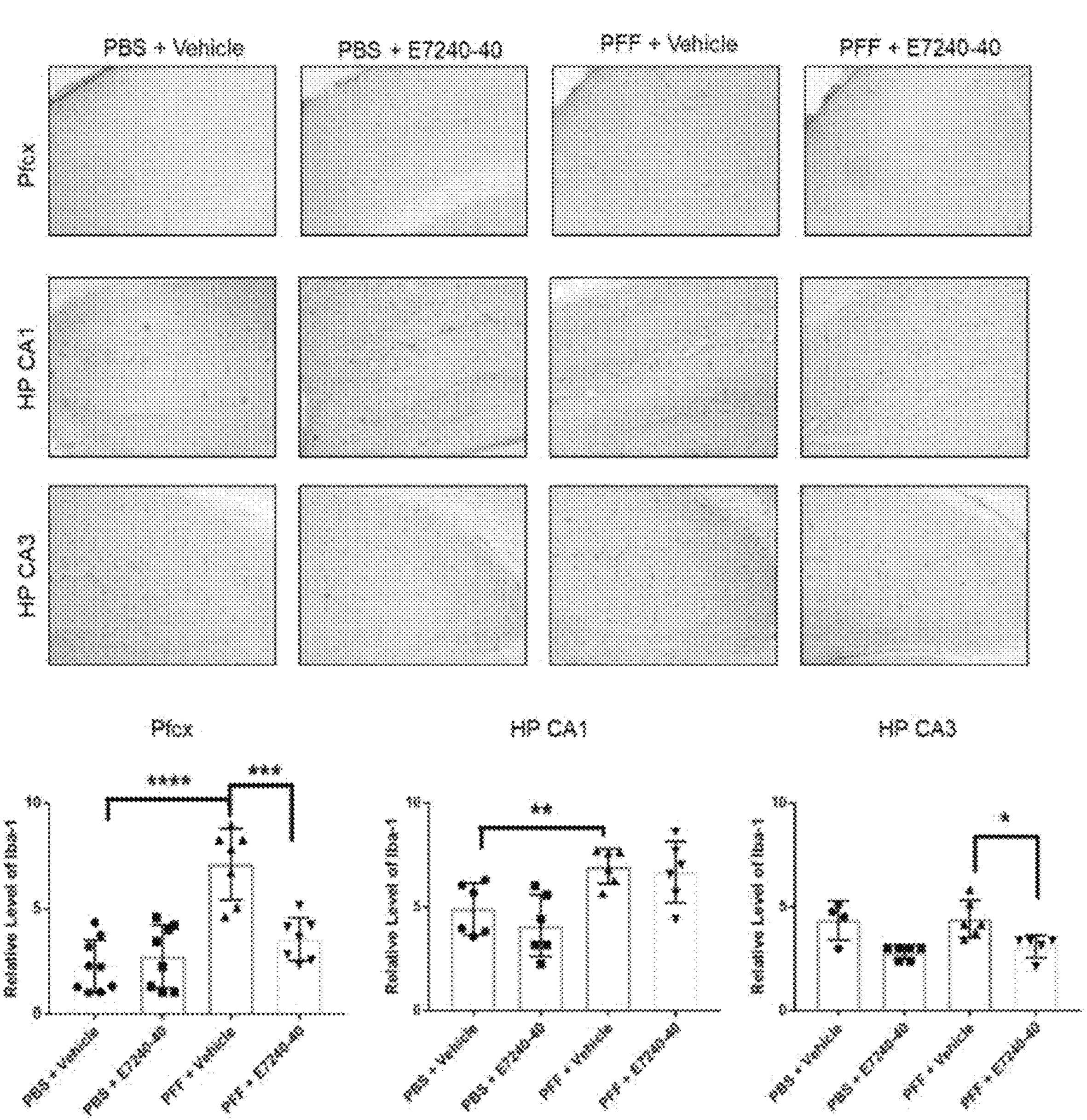
FIG. 13 shows results of microglia pathology of PFF-injected mice according to the administration of the compound of Example 2.

In addition, as shown in FIG. 13, the compound of Example 2 improved microglia pathology in PFF-injected mice. The single inoculation of PFF within the dorsal striatum increased Iba1 immunoreactivity in both the Pfcx and hippocampus (HP CA1). The administration of the compound of Example 2 for 3 months reduced Iba1 immunopositive activated microglia in Pfcx and HP CA3.

Figure 14:
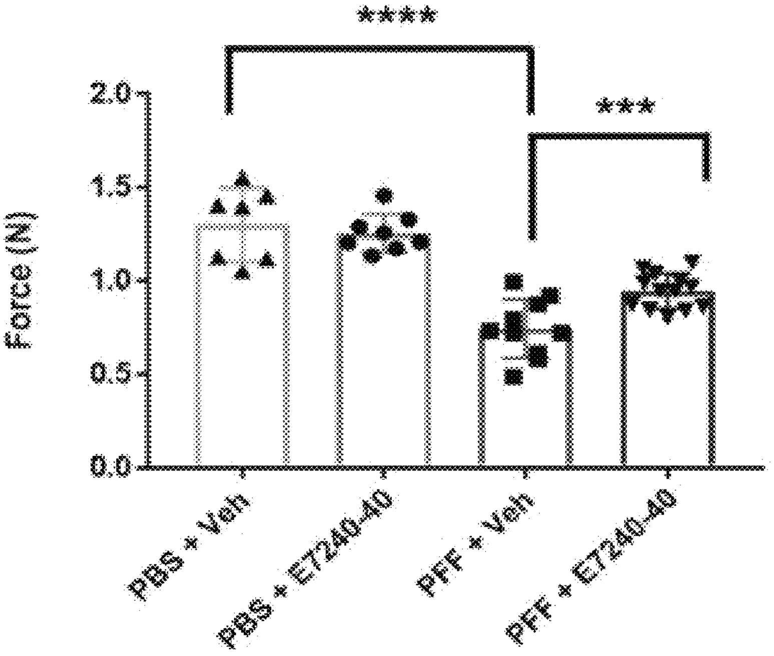
FIG. 14 shows the degree of improvement in neuromuscular function of PFF-injected mice according to the administration of the compound of Example 2.

Finally, as shown in FIG. 14, the compound of Example 2 improved the neuromuscular function of PFF-injected mice. The maximum force of the mouse forelimb was recorded with a grip strength meter. The single inoculation of PFF impaired the grip strength of the forelimb. The 3-month treatment with the compound of Example 2 improved the grip strength of PFF-injected mice.

It was confirmed from the above results that the compounds according to the present invention had excellent Nox inhibitory effect and excellent antioxidant effect. Further, it was confirmed that the compound according to the present invention exhibited excellent effects particularly in the prevention and treatment of degenerative brain diseases.

Experimental Example 5. Treatment of Compound of Example 1 for Diabetic Retinopathy (DR) and Age-Related Macular Degeneration (AMD)

(1) Experiment Method

Choroidal neovascularization (CNV) was induced in 7-week-old female C57BL/6 mice by laser photocoagulation (200 mW, 80 ms duration, 4 spots). Mice were divided into 5 groups.

(1) Naive Group (2) Vehicle Group (Laser and Vehicle Injection)

(3) Aflibercept 1 μg group (laser and intravitreal injection of 1 μg aflibercept)

(4) Aflibercept 20 μg group (laser and intravitreal injection of 20 μg aflibercept)

(5) Example 1 compound group (laser and 5 μl of Example 1 compound (1 mg/ml), eye drops).

One day post laser injury, mice were intravitreally injected with 1 μl of aflibercept (1 mg/ml or 20 mg/ml). 5 μl of the compound of Example 1 (1 mg/ml) was instilled into the eye 4 times a day for 12 days starting from the day of laser injury. On Day 12 after laser photocoagulation, the area of choroidal neovascularization was measured using fundus fluorescein angiography and histopathological assay. Visual function was evaluated by electrophoresis. Apoptotic cells are detected by TUNEL staining. VEGF and GFAP were detected by immunofluorescence staining.

(2) Experimental Results According to Administration of the Compound of Example 1

Figure 15:
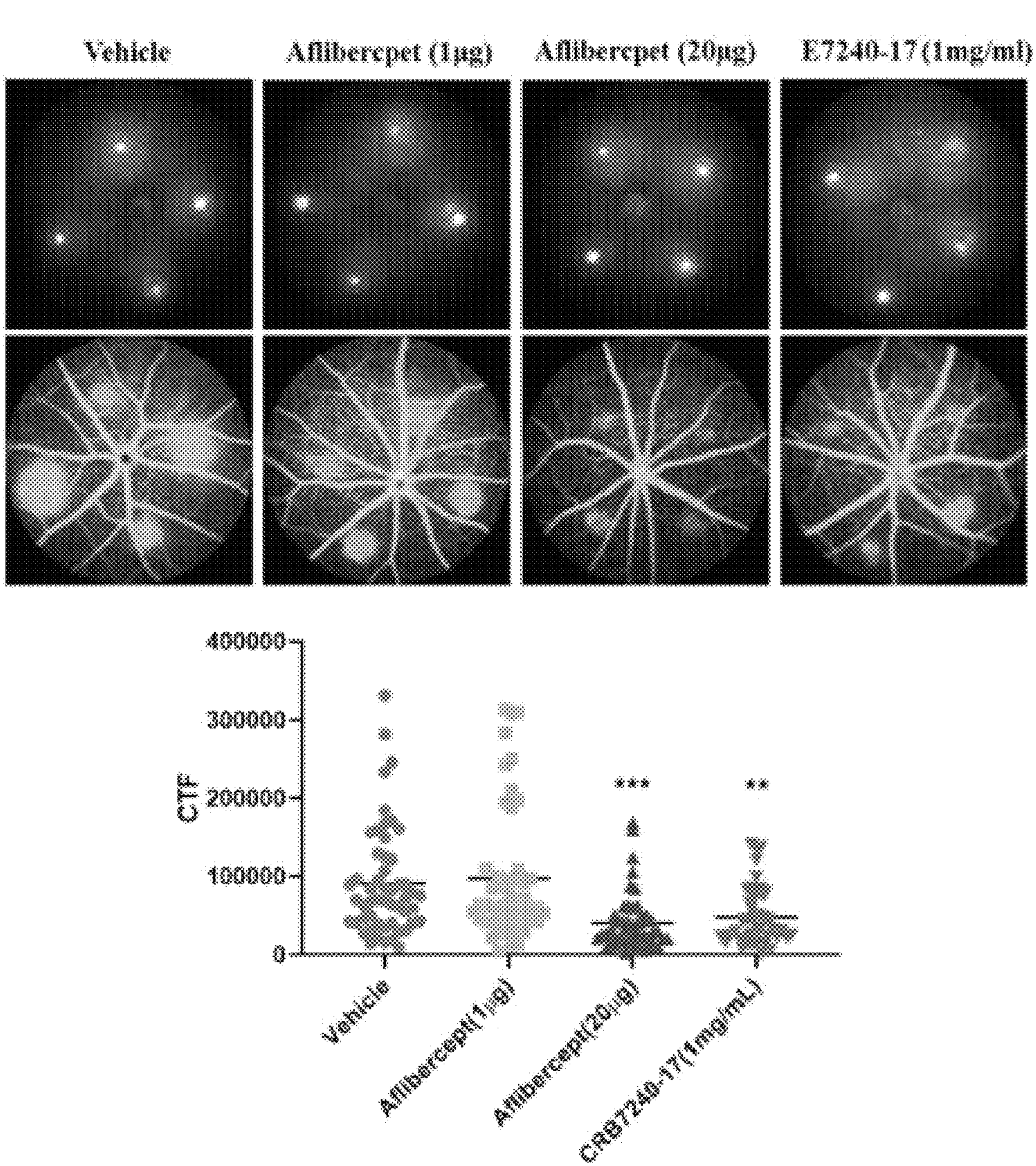
FIG. 15 shows results of laser-induced choroidal neovascularization (CNV) inhibition according to the administration of the compound of Example 1.

As shown in FIG. 15, the compound of Example 1 (E7240-17) inhibited laser-induced choroidal neovascularization (CNV). Administration of the compound of Example 1 (1 mg/ml, 5 μl, 4 times/day, for 12 days) by eye drop significantly reduced choroidal neovascularization vascular leakage with efficacy similar to that of intravitreal injection of 20 μg aflibercept.

Figure 16:
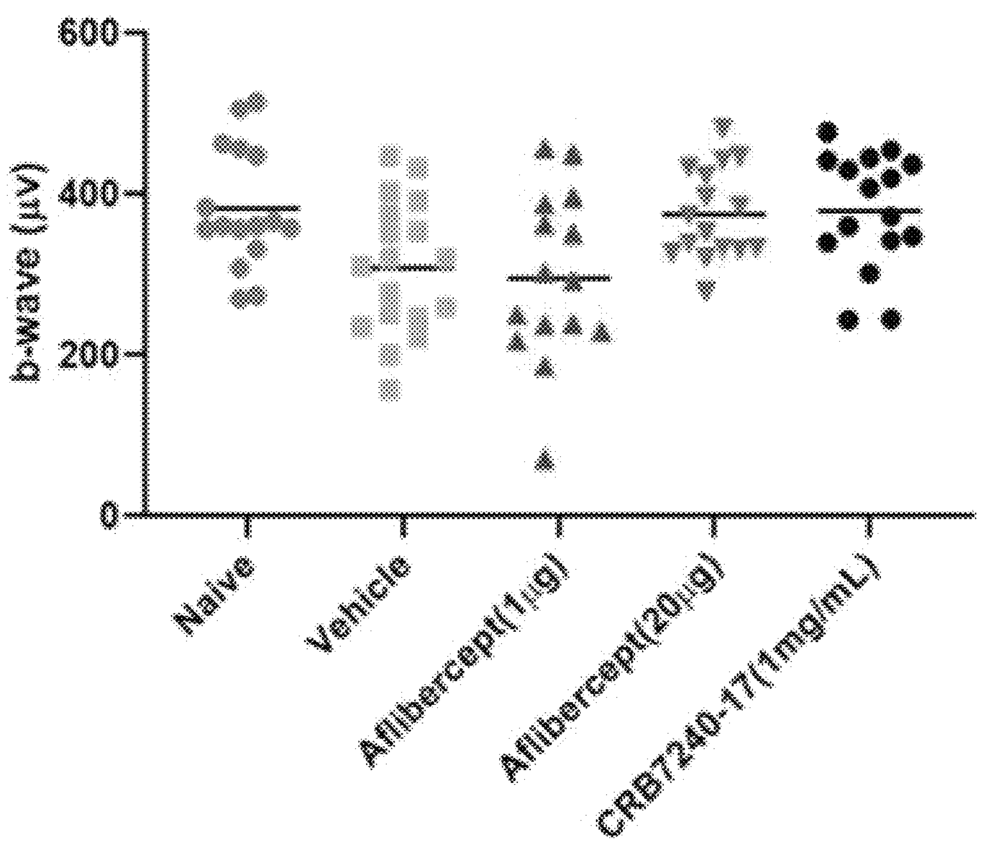
FIG. 16 shows results of enhancement of post-synaptic function according to the administration of the compound of Example 1.

Also, as shown in FIG. 16, the compound of Example 1 improved postsynaptic function. On Day 13 after injury, the b-wave amplitude in the vehicle group was lower than that in the naive group, but eye drops of the compound of Example 1 improved the b-wave amplitude, similar to intravitreal injection of 20 μg aflibercept.

Figure 17:
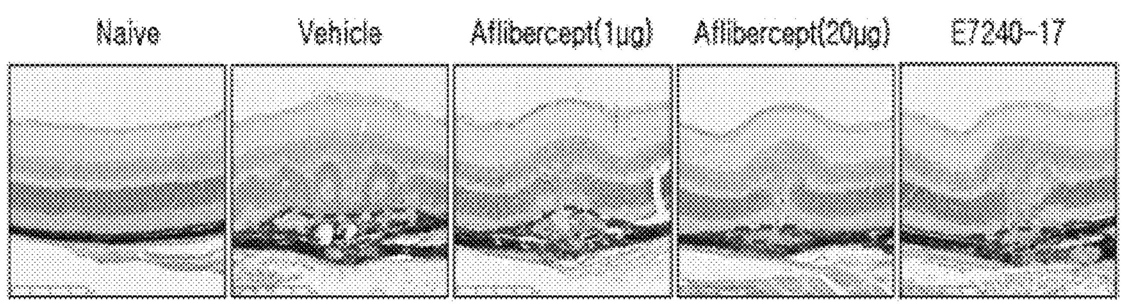
FIG. 17 shows results of attenuation of laser photocoagulation-induced CNV lesion according to the administration of the compound of Example 1.

Meanwhile, as shown in FIG. 17, the compound of Example 1 attenuated CNV lesions induced by laser photocoagulation. Hematoxylin and eosin staining was performed to study the histology of CNV lesions. The lesion size of the compound group of Example 1 was significantly smaller than that of the vehicle group.

Figure 18:
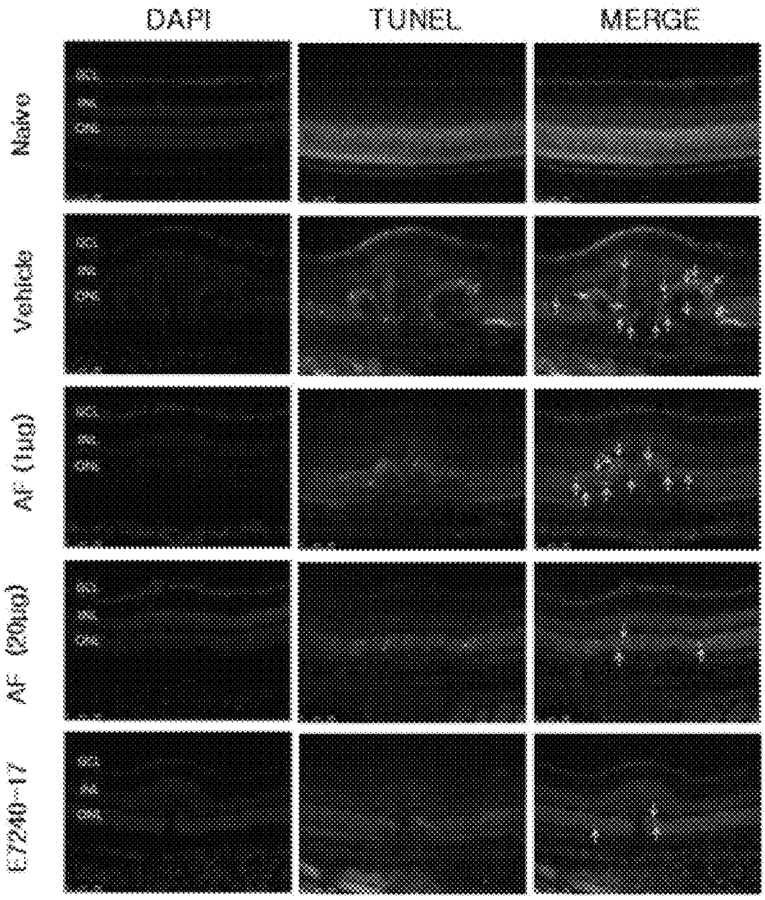
FIG. 18 shows results of inhibition of laser photocoagulation-induced cell death according to the administration of the compound of Example 1.

Meanwhile, as shown in FIG. 18, the compound of Example 1 inhibited cell death induced by laser photocoagulation. Mouse eye sections were stained with TdT-UDP nick end labeling. Even though TUNEL-positive cells significantly increased in the vehicle-treated group, eye drops of the compound of Example 1 dramatically reduced TUNEL-positive cells, similar to intravitreal injection of 20 μg aflibercept. Yellow arrows indicate TUNEL-positive cells.

Figure 19:
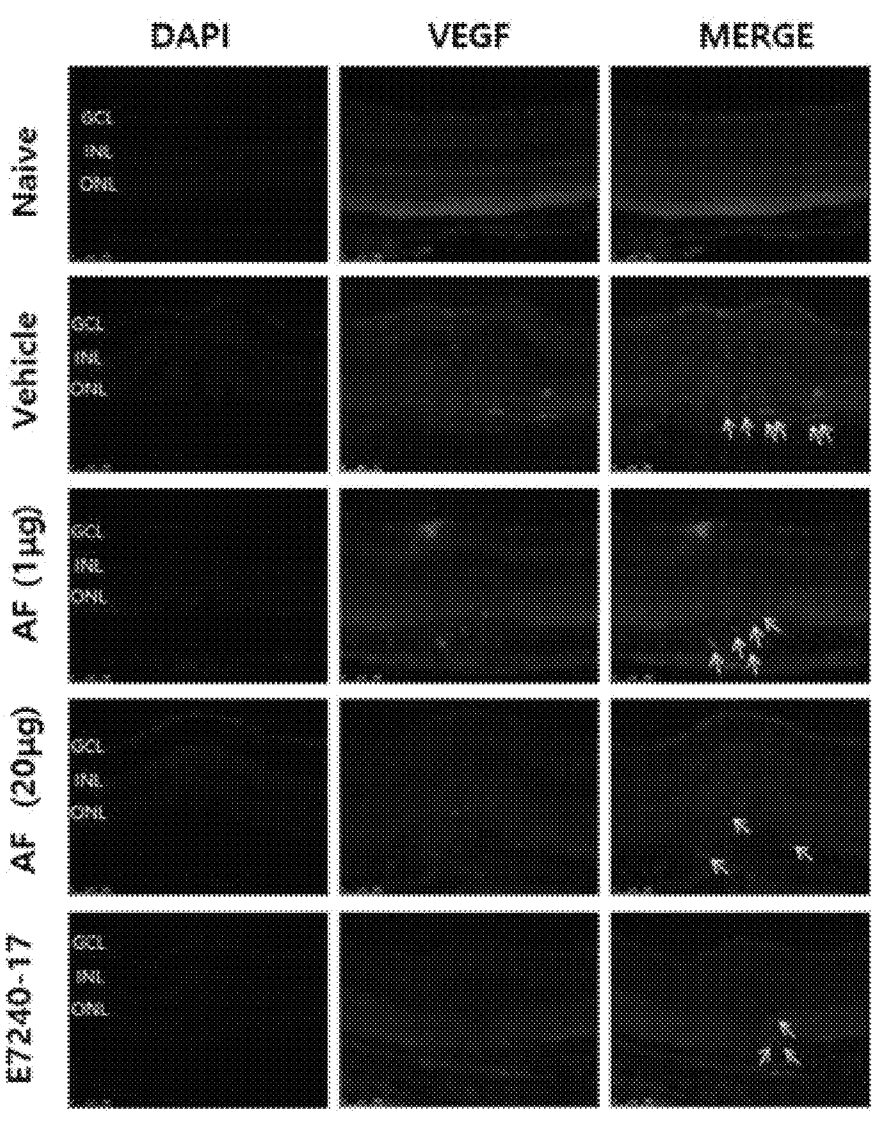
FIG. 19 shows results of inhibition of vascular endothelial growth factor (VEGF) expression according to the administration of the compound of Example 1.

As shown in FIG. 19, the compound of Example 1 inhibited vascular endothelial growth factor (VEGF) expression. Eye sections were immunofluorescently stained with an anti-VEGF antibody. Immunolabeling of VEGF increased in CNV in the vehicle-treated group. However, eye drops of the compound of Example 1 dramatically reduced VEGF expression, similar to intravitreal injection of 20 μg aflibercept. Yellow arrows indicate VEGF-positive cells.

Figure 20:
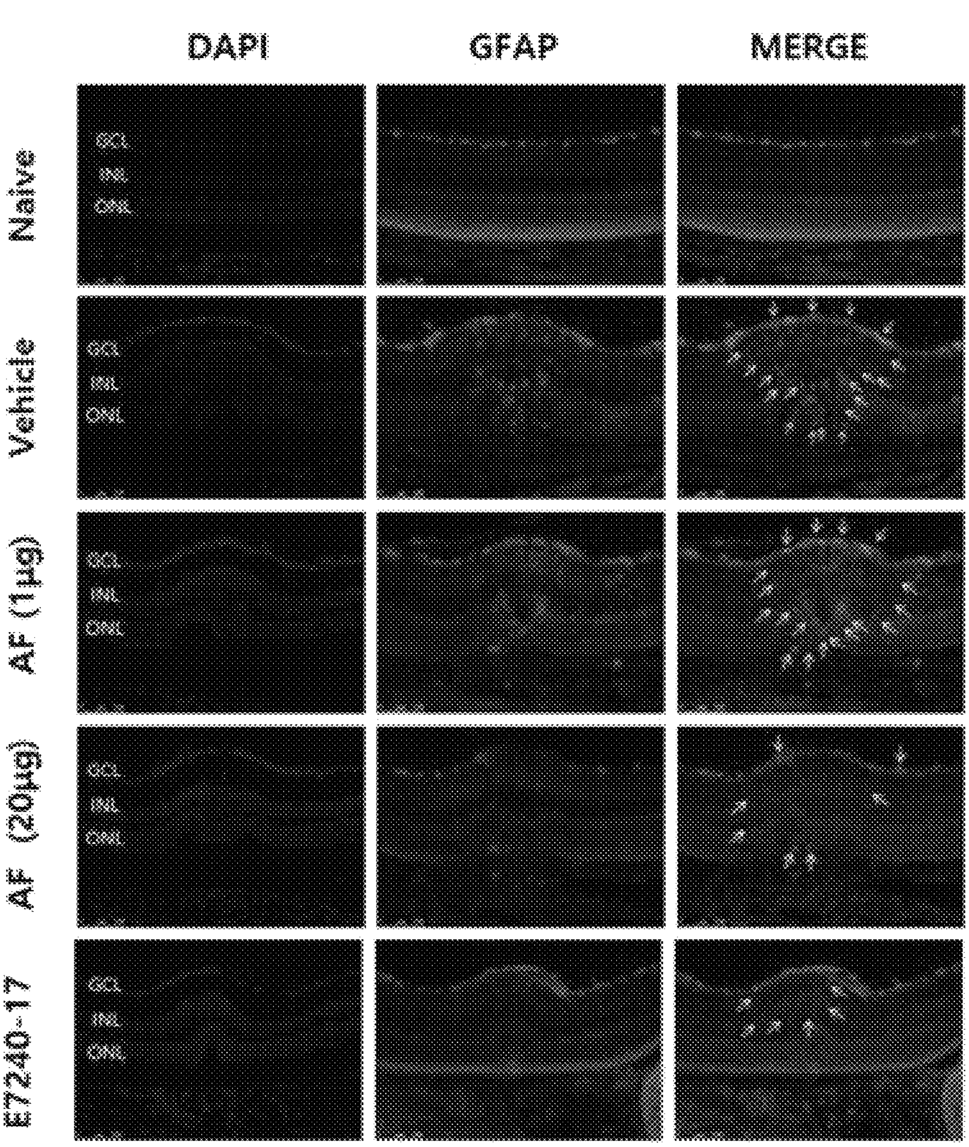
FIG. 20 shows results of improvement in activation of Müller cells and astrocytes according to the administration of the compound of Example 1.

Finally, as shown in FIG. 20, the compound of Example 1 improved the activation of Müller cells and astrocytes. Activation of Müller cells and astrocytes was observed by immunostaining using an anti-GFAP antibody. On Day 13 post CNV, activation of Müller cells and astrocytes was observed in the vehicle group. However, eye drops of the compound of Example 1 significantly improved activation of Müller cells and astrocytes, similar to intravitreal injection of 20 μg aflibercept. Yellow arrows indicate GFAP-positive cells.

It was confirmed from the above results that the compounds according to the present invention had excellent Nox inhibitory effect and excellent antioxidant effect. Further, it was confirmed that the compounds according to the present invention exhibited excellent effects particularly in the prevention and treatment of retinal diseases.

As described above, the present invention has been described through Examples. Those skilled in the art to which the present disclosure pertains will understand that the present disclosure may be embodied in other specific forms without changing the technical spirit or essential characteristics thereof. Therefore, the above-described Examples should be understood as illustrative in all aspects and not limiting. The scope of the present disclosure is indicated by the following claims rather than the detailed description, and should be construed as including all changes or modifications derived from the meaning and scope of the claims and equivalent concepts within the scope of the present invention.

The invention claimed is:

1. A compound represented by the following Chemical Formula 3:

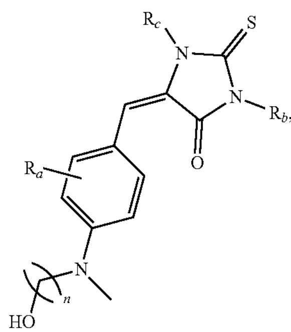

wherein $R_a$ is hydrogen, a hydroxyl group or a $C_1$-$C_4$ alkoxy group, $R_b$ is a $C_1$-$C_6$ straight chain or branched chain alkyl group, a $C_3$-$C_{10}$ cycloalkyl group, or a —($C_1$-$C_3$ alkyl) $C_6$-$C_{12}$ aryl group, $R_c$ is hydrogen or a $C_1$-$C_4$ alkyl group, and n is any integer from 1 to 4.

2. The compound of claim 1, wherein the compound represented by Chemical Formula 3 is a compound represented by the following Chemical Formula 4:

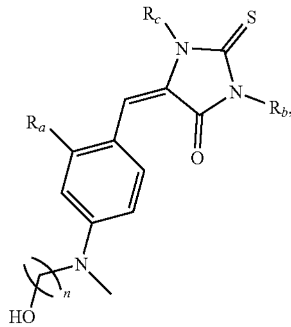

wherein $R_a$ is hydrogen, a hydroxyl group or a $C_1$-$C_4$ alkoxy group, $R_b$ is a $C_1$-$C_6$ straight chain or branched chain alkyl group, a $C_3$-$C_{10}$ cycloalkyl group, or a —($C_1$-$C_3$ alkyl) $C_6$-$C_{12}$ aryl group, $R_c$ is hydrogen or a $C_1$-$C_4$ alkyl group, and n is any integer from 1 to 4.

3. The compound of claim 1, wherein $R_a$ is hydrogen, hydroxy, methoxy, or ethoxy.

4. The compound of claim 1, wherein $R_b$ is any one selected from the group consisting of methyl, ethyl, propyl, isopropyl, isobutyl, sec-butyl, tert-butyl, pentyl, isopentyl, neopentyl, sec-pentyl, tert-pentyl, hexyl, cyclopentyl, cyclohexyl, cycloheptyl, cyclooctyl, benzyl, and phenethyl.

5. The compound of claim 4, wherein $R_b$ is any one selected from the group consisting of isobutyl, cyclohexyl, benzyl, and phenethyl.

6. The compound of claim 1, wherein $R_c$ is any one selected from the group consisting of hydrogen, methyl, ethyl, propyl, isopropyl, isobutyl, sec-butyl, and tert-butyl.

7. The compound of claim 1, wherein $R_a$ is hydrogen, hydroxy, methoxy, or ethoxy, $R_b$ is any one selected from the group consisting of isobutyl, cyclohexyl, benzyl, and phenethyl, $R_c$ is hydrogen, methyl, or ethyl, and n is 1, 2 or 3.

8. The compound of claim 1, wherein the compound represented by Chemical Formula 3 is any one selected from the group consisting of the following compounds:

(E)-3-cyclohexyl-5-(4-((2-hydroxyethyl)(methyl)amino)benzylidene)-1-methyl-2-thioxoimidazolidin-4-one;

(E)-5-(4-((2-hydroxyethyl)(methyl)amino)benzylidene)-3-isobutyl-1-methyl-2-thioxoimidazolidin-4-one;

(Z)-5-(4-((2-hydroxyethyl)(methyl)amino)benzylidene)-3-isobutyl-1-methyl-2-thioxoimidazolidin-4-one;

(E)-3-cyclohexyl-5-(4-((2-hydroxyethyl)(methyl)amino)-2-methoxybenzylidene)-1-methyl-2-thioxoimidazolidin-4-one;

(E)-3-cyclohexyl-5-(2-hydroxy-4-((2-hydroxyethyl)(methyl)amino)benzylidene)-1-methyl-2-thioxoimidazolidin-4-one;

(E)-3-benzyl-5-(4-((3-hydroxypropyl)(methyl)amino)benzylidene)-1-methyl-2-thioxoimidazolidin-4-one;

(E)-5-(4-((2-hydroxyethyl)(methyl)amino)benzylidene)-1-methyl-3-phenethyl-2-thioxoimidazolidin-4-one;

(E)-3-benzyl-5-(2-hydroxy-4-((2-hydroxyethyl)(methyl)amino)benzylidene)-1-methyl-2-thioxoimidazolidin-4-one; and;

(E)-3-benzyl-5-(4-((3-hydroxypropyl)(methyl)amino)-2-methoxybenzylidene)-1-methyl-2-thioxoimidazolidin-4-one.

9. A method for treating NADPH oxidase (NOX)-associated diseases comprising: administering, to a subject in need thereof, a therapeutically effective amount of a compound represented by the following Chemical Formula 3, an isomer or a pharmaceutically acceptable salt thereof:

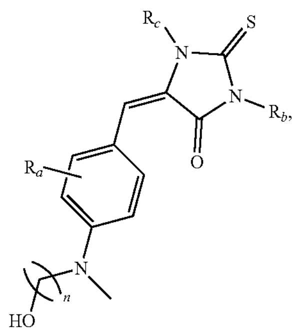

wherein $R_a$ is hydrogen, a hydroxyl group or a $C_1$-$C_4$ alkoxy group, $R_b$ is a $C_1$-$C_6$ straight chain or branched chain alkyl group, a $C_3$-$C_{10}$ cycloalkyl group, or a —($C_1$-$C_3$ alkyl) $C_6$-$C_{12}$ aryl group, $R_c$ is hydrogen or a $C_1$-$C_4$ alkyl group, and n is any integer from 1 to 4, wherein the NADPH oxidase (NOX)-associated disease is any one selected from the group consisting of psoriasis, rheumatoid arthritis, osteoarthritis, restenosis, atherosclerosis, ulcers, liver cirrhosis, glomerulonephritis, diabetic nephropathy, malignant nephrosclerosis, thrombotic microangiopathy, organ transplant rejection, diabetes, hypertension, cardiac hypertrophy, heart failure, cancer, autoimmune diseases, inflammatory diseases, degenerative brain diseases, and retinal diseases.

10. The method of claim 9, wherein the degenerative brain disease is any one selected from the group consisting of Parkinson's disease, Huntington's disease, Alzheimer's disease, mild cognitive impairment, senile dementia, amyotrophic lateral sclerosis, spinocerebellar atrophy, Tourette's syndrome, Friedrich's ataxia, Machado-Joseph's disease, Lewy body dementia, dystonia, progressive supranuclear palsy, and frontotemporal dementia.

11. The method of claim 9, wherein the retinal disease is any one selected from the group consisting of glaucoma, proliferative vitreoretinopathy, diabetic retinopathy, macular degeneration, choroidal neovascularization, and retinal edema.

12. A pharmaceutical composition comprising: the compound of claim 1, an isomer or a pharmaceutically acceptable salt thereof; and a pharmaceutically acceptable carrier.

13. The method of claim 9, wherein $R_a$ is hydrogen, hydroxy, methoxy, or ethoxy.

14. The method of claim 9, wherein $R_b$ is any one selected from the group consisting of methyl, ethyl, propyl, isopropyl, isobutyl, sec-butyl, tert-butyl, pentyl, isopentyl, neopentyl, sec-pentyl, tert-pentyl, hexyl, cyclopentyl, cyclohexyl, cycloheptyl, cyclooctyl, benzyl, and phenethyl.

15. The method of claim 13, wherein $R_b$ is any one selected from the group consisting of isobutyl, cyclohexyl, benzyl, and phenethyl.

16. The method of claim 9, wherein $R_c$ is any one selected from the group consisting of hydrogen, methyl, ethyl, propyl, isopropyl, isobutyl, sec-butyl, and tert-butyl.

17. The method of claim 9, wherein $R_a$ is hydrogen, hydroxy, methoxy, or ethoxy, $R_b$ is any one selected from the group consisting of isobutyl, cyclohexyl, benzyl, and phenethyl, $R_c$ is hydrogen, methyl, or ethyl, n is 1, 2 or 3, and m is 1.

18. The method of claim 9, wherein the compound represented by Chemical Formula 3 is any one selected from the group consisting of the following compounds:

(E)-3-cyclohexyl-5-(4-((2-hydroxyethyl)(methyl)amino)benzylidene)-1-methyl-2-thioxoimidazolidin-4-one;

(E)-5-(4-((2-hydroxyethyl)(methyl)amino)benzylidene)-3-isobutyl-1-methyl-2-thioxoimidazolidin-4-one;

(Z)-5-(4-((2-hydroxyethyl)(methyl)amino)benzylidene)-3-isobutyl-1-methyl-2-thioxoimidazolidin-4-one;

(E)-3-cyclohexyl-5-(4-((2-hydroxyethyl)(methyl)amino)-2-methoxybenzylidene)-1-methyl-2-thioxoimidazolidin-4-one;

(E)-3-cyclohexyl-5-(2-hydroxy-4-((2-hydroxyethyl)(methyl)amino)benzylidene)-1-methyl-2-thioxoimidazolidin-4-one;

(E)-3-benzyl-5-(4-((3-hydroxypropyl)(methyl)amino)benzylidene)-1-methyl-2-thioxoimidazolidin-4-one;

(E)-5-(4-((2-hydroxyethyl)(methyl)amino)benzylidene)-1-methyl-3-phenethyl-2-thioxoimidazolidin-4-one;

(E)-3-benzyl-5-(2-hydroxy-4-((2-hydroxyethyl)(methyl)amino)benzylidene)-1-methyl-2-thioxoimidazolidin-4-one; and;

(E)-3-benzyl-5-(4-((3-hydroxypropyl)(methyl)amino)-2-methoxybenzylidene)-1-methyl-2-thioxoimidazolidin-4-one.

* * * * *